(12) United States Patent
Tao et al.

(10) Patent No.: US 7,816,346 B2
(45) Date of Patent: Oct. 19, 2010

(54) ANALOGS OF ANSAMYCIN AND PHARMACEUTICAL COMPOSITIONS THEREOF

(75) Inventors: Chunlin Tao, Los Angeles, CA (US); Hongna Han, Los Angeles, CA (US); Xiaowen Sun, Los Angeles, CA (US); Neil Desai, Los Angeles, CA (US); Patrick Soon-Shiong, Los Angeles, CA (US)

(73) Assignee: Abraxis BioScience, LLC, Los Angeles, CA (US)

( * ) Notice: Subject to any disclaimer, the term of this patent is extended or adjusted under 35 U.S.C. 154(b) by 148 days.

(21) Appl. No.: 11/940,644

(22) Filed: Nov. 15, 2007

(65) Prior Publication Data

US 2008/0234246 A1 Sep. 25, 2008

Related U.S. Application Data

(60) Provisional application No. 60/865,977, filed on Nov. 15, 2006.

(51) Int. Cl.
C07D 225/06 (2006.01)
C07D 401/12 (2006.01)
A61K 31/395 (2006.01)

(52) U.S. Cl. ...................... 514/183; 540/461
(58) Field of Classification Search ............ 540/461; 514/183
See application file for complete search history.

(56) References Cited

U.S. PATENT DOCUMENTS

| 4,075,339 | A | 2/1978 | Rinehart, Jr. et al. |
| 5,916,596 | A | 6/1999 | Desai et al. |
| 6,506,405 | B1 | 1/2003 | Desai et al. |
| 6,537,579 | B1 | 3/2003 | Desai et al. |

FOREIGN PATENT DOCUMENTS

WO    WO 94/08578 A2    4/1994

OTHER PUBLICATIONS

Bedin et al., *Int. J. Cancer*, 109, 643-652 (2004).
Dasgupta et al., *Exp. Cell. Res.*, 237, 29-37 (1997).
Deboer et al., *J. Antibiotics*, 442-447 (Sep. 1970).
Li et al., *Antimicrobial Agents and Chemotherapy*, 48 (3), 867-872 (Mar. 2004).
Machida et al., *Int. J. Radiat. Biol.*, 79 (12), 973-980 (Dec. 2003).
Mandler et al., *Cancer Res.*, 64, 1460-1467 (Feb. 15, 2004).
McLean et al., *Biochem. and Biophys. Res. Comm.*, 321, 665-669 (2004).
Muise-Helmericks et al., *J. Biol. Chem.*, 273 (45), 29864-29872 (1998).
Panaretou et al., *EMBO J.*, 17 (16), 4829-4836 (1998).
Prodromou et al., *Cell*, 90, 65-75, (Jul. 11, 1997).
Scheibel et al., *Proc. Natl. Acad. Sci. USA*, 96, 1297-1302 (Feb. 1999).
Sepehrnia et al., *J. Biol. Chem.*, 271 (25), 15084-15090 (1996).
Stebbins, et al., *Cell*, 89, 239-250 (Apr. 18, 1997).
Subbarao et al., *Pharmacology & Therapeutics*, 101, 227-257 (2004).
Vasilevskaya et al., *Cancer Res.*, 59, 3935-3940 (Aug. 15, 1999).
Whitesell et al., *Current Cancer Drug Targets*, 3, 349-358 (2003).
Workman, Paul., *Trends in Mol. Med.*, 10 (2), 47-51 (Feb. 2004).
Li et al., *Chemical Abstracts Service*, Accession No. 1977:545543 (1977).
Rinehart et al., *Chemical Abstracts Service*, Accession No. 1978:152557 (1977).
Schnur et al., *J. Med. Chem.*, 38, 3806-3812 (1995).
Search Report PCT/US2007/084662 (Feb. 29, 2008).

*Primary Examiner*—Bruck Kifle
(74) *Attorney, Agent, or Firm*—Leydig, Voit & Mayer, Ltd.

(57) ABSTRACT

Analogs of geldanamycin (an ansamycin), pharmaceutical formulations comprising such analogs, and methods of use (e.g., treating tumors).

13 Claims, No Drawings

ANALOGS OF ANSAMYCIN AND PHARMACEUTICAL COMPOSITIONS THEREOF

CROSS-REFERENCE TO RELATED APPLICATIONS

This patent application claims the benefit of U.S. Provisional Patent Application No. 60/865,977 filed Nov. 15, 2006, which is incorporated by reference.

BACKGROUND OF THE INVENTION

Geldanamycin (GM) is a benzoquinone ansamycin polylketide isolated from *Streptomyces hygroscopicus*. See DeBoer et al., *Antibiot.*, 1970, 23, 442.

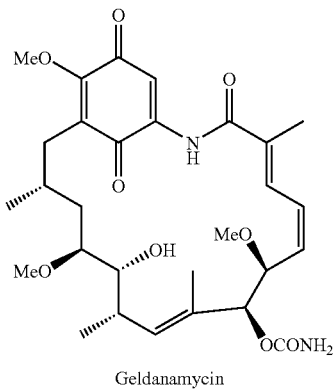

Geldanamycin

Although originally discovered by screening microbial extracts for antibacterial and antiviral activity, geldanamycin was later found to be cytotoxic to certain tumor cells. It is reported that geldanamycin exerts its antiproliferative and anti-cancer effect by binding with the heat shock protein 90 (Hsp90) chaperone and, in turn, altering the translocation properties of the tumor suppressor protein p53. See Stebbins et al., *Cell*, 1997, 239; Sepehrnia et al., *J. Biol. Chem.*, 1996, 271, 15, 084; Dasgupta et al., *Experimental Cell Research*, 1997, 29, 237.

Inhibition of Hsp90 results in interference in multiple signaling pathways that mediate cancer growth and cell survival. Hsp90 is essential for the stability and function of several oncogenic proteins associated with key sites of genetic deregulation in human cancer. It is known to be over-expressed in human tumors and has the potential to inhibit the hallmark traits of cancer such as cell growth, signaling apoptosis avoidance, limitless proliferation, angiogenesis, and metastasis. See Sreedhar et al, *Pharmacology & Therapeutics*, 2004, 101, 227.

Geldanamycin was thought to exert its anti-cancerous effects by tight binding of the N-terminus pocket of Hsp90s. See Stebbins, C. et al., *Cell*, 1997, 89, 239. Further, ATP and ADP have both been shown to bind this pocket with low affinity and to have weak ATPase activity. See Proronlou, C. et al., *Cell*, 1997, 90, 65; Panaretou et al., *EMBO J*, 1998, 17, 4829. In vitro and in vivo studies have demonstrated that occupancy of this N-terminal pocket by geldanamycins and other Hsp90 inhibitors alters Hsp90 function and inhibits protein folding. At high concentrations, geldanamycins and other Hsp90 inhibitors have been shown to prevent binding of protein substrates to Hsp90 and to inhibit the ATP-dependent release of chaperone-associated protein substrates. See Scheibel et al., *Proc. Nat'l. Acad. Sci. USA*, 1999, 96, 1297. The geldanamycin-induced loss of these proteins leads to selective disruption of certain regulatory pathways and results in growth arrest at specific phases of the cell cycle. (See Muise-Heimericks et al., *J Biol. Chem.*, 1998, 273, 29864), apoptosis, and/or differentiation of cells. See Vasilevskaya et al., *Cancer Res.*, 1999, 59, 3935.

Recently, geldanamycin, as a specific inhibitor of Hsp90, was found to diminish specific wild-type p53 binding to the p21 promoter sequence. See McLean et al., *Biochem Biophys Res Commun.* 2004, 321(3), 665. Consequently, these inhibitors decrease p21 mRNA levels, which lead to a reduction in cellular p21/Waf1 protein, the latter being known to induce cell cycle arrest. A minor decrease in p53 protein levels following the treatment of human fibroblasts with the inhibitors suggests the potential involvement of Hsp90 in the stabilization of wild-type p53. More recently, geldanamycin was found to induce Hsp70 and prevent alpha-synuclein aggregation and toxicity in vitro. See McLean et al., *Biochem Biophys Res Commun.* 2004, 321(3), 665.

An important property of Hsp90 inhibitors is their ability to cause simultaneous combinatorial blockade of multiple cancer-causing pathways by promoting the degradation of many oncogenic client proteins. See Workman P., *Trends Mol. Med.* 2004 10(2), 47. Bedin et al. reported that geldanamycin induces MAPK-independent cell cycle arrest by inhibiting the chaperone function of the Hsp90 protein through competition for ATP binding. See Bedin et al., *J. Int. J. Cancer* 2004, 9(5), 43. The antiproliferative effect of geldanamycin has been attributed to destabilization of the Raf-1 protein, one of the targets of Hsp90, and to the resulting inhibition of MAPK. Li et al. found that geldanamycin exhibits broad-spectrum antiviral activity, including HSV-1 and severe acute respiratory syndrome coronavirus. Li et al., *Antimicrob. Agents Chemother.* 2004, 48(3), 867. HSV-1 replication in vitro was significantly inhibited by geldanamycin with a 50% inhibitory concentration of 0.093 µM which was also a concentration that inhibited cellular growth 50% in comparison with the results seen with untreated controls of 350 µM. The therapeutic index of geldanamycin was found to be over 3700.

Mandler et al. reported that conjugating geldanamycin to the anti-HER2 mAb Herceptin in targeted cancer therapy resulted in a greater antitumor effect than Herceptin alone. See Mandler et al. *Cancer Res.* 2004, 64(4), 1460. Geldanamycin also was to enhance the radiation sensitivity of human tumor cells by inhibiting the EGFR signal transduction system and the Akt signaling pathway. See Machida et al., *Int. J. Radiat. Biol.* 2003, 79(12), 973.

Despite its therapeutic potential as an anticancer agent, initial studies have indicated that the bioavailability of geldanamycin must be enhanced and the toxicity associated with the natural product reduced before significant progress can be made with respect to the therapeutic use of geldanamycin. The association of hepatotoxicity with the administration of geldanamycin led to its withdrawal from Phase I clinical trials. As with several other promising anticancer agents, geldanamycin also has poor water solubility that makes it difficult to deliver in therapeutically effective doses.

Analogues of geldanamycin have been synthesized in an attempt to increase the bioavailability and reduce the toxicity associated with the natural product. Among the more successful analogues is 17-allylaminogeldanamycin (17-AAG), which is currently in phase II clinical trials at the National Cancer Institute.

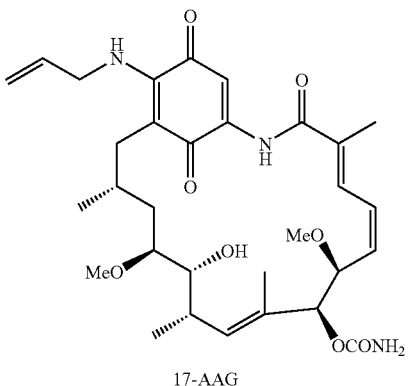

17-AAG

17-AAG has shown reduced hepatotoxicity while maintaining Hsp90 binding. This compound was selected for clinical studies based on its in vitro activity against chemorefractory tumors and novel biological actions. Like geldanamycin, 17-AAG has limited aqueous solubility. This property requires the use of a solubilizing carrier, most commonly Cremophore®, a polyethoxylated castor oil; however Cremophore® can produce serious side reactions in some patients.

A deficiency of the previous generation of ansamycins, such as geldanamycin and 17-AAG, is that they exhibit one or more poor pharmacological properties, e.g., metabolic instability, poor bioavailability, and/or difficult formulation ability, particularly for in vivo intravenous administration.

Therefore, there remains a need to prepare and synthesize anti-cancer compounds that allow for administration of doses significantly below the maximum tolerated dose while maintaining therapeutic effectiveness, as well as appropriate dosing schedules for combination therapy. The present invention provides these and other advantages.

BRIEF SUMMARY OF THE INVENTION

The invention provides reduced forms of benzoquinone imine-containing ansamycins, and its acylation or alkylation derivatives, and uses of them in the treatment of diseases or conditions characterized by undesired cellular proliferation or hyperproliferation.

In one embodiment, the present invention provides a pure and isolated compound of formula (I):

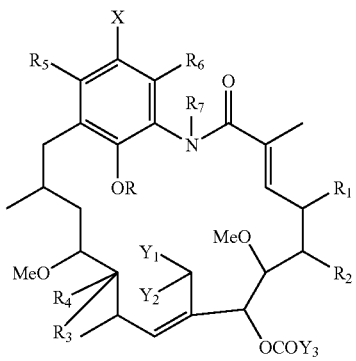

wherein

X is selected from the group consisting of —N($R_8$)($R_9$), —N($R_8$)—C(O)$R_{10}$, —N($R_8$)—C(O)—O$R_{10}$, —N($R_8$)—C(O)—N$R_8R_{10}$, —N($R_8$)—SO$_2R_{10}$, —N($R_8$)—C(S)O$R_{10}$, —N($R_8$)—C(S)—O$R_{10}$, and —N($R_8$)—C(S)—N$R_8R_{10}$;

wherein $R_8$ and $R_9$ are independently selected from the group consisting of H, optionally substituted ($C_1$-$C_{20}$) alkyl, optionally substituted ($C_2$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkynyl, optionally substituted aryl, optionally substituted heteroaryl, optionally substituted arylalkyl, optionally substituted heteroarylalkyl, optionally substituted cycloalkyl, and optionally substituted cycloheteroalkyl; $R_8$ is selected from the group consisting of H, optionally substituted ($C_1$-$C_6$) alkyl, optionally substituted ($C_5$-$C_8$) aryl, and an optionally substituted ($C_5$-$C_8$) heteroaryl, or together with $R_9$ form an optionally substituted 4-7 membered heterocyclic or carbocyclic ring; $R_{10}$ is selected from the group consisting of hydrogen, an optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkynyl, optionally substituted ($C_6$-$C_{20}$) aryl, optionally substituted ($C_3$-$C_{20}$) heteroaryl, optionally substituted ($C_7$-$C_{20}$) arylalkyl, optionally substituted ($C_4$-$C_{20}$) heteroarylalkyl, optionally substituted ($C_3$-$C_{20}$) cycloalkyl, and an optionally substituted ($C_2$-$C_{20}$) cycloheteroalkyl;

R represents, hydrogen, substituted or unsubstituted ($C_1$-$C_6$) alkyl or ($C_1$-$C_6$) alkenyl or ($C_6$-$C_{10}$) aryl or COR$_8$.

$R_1$ and $R_2$ are each a hydrogen or $R_1$ and $R_2$ together form a single bond;

$R_3$, $R_4$, $Y_1$, $Y_2$, $Y_3$ are independently selected from the group consisting H, halo, —OH, O-alkyl, O-acetyl, —O-aryl, OC(O)$R_{10}$, —SO$_2$—$R_{10}$, and —NHR$_{10}$, or together form oxo (=O), or hydroxylamino alkoxyimine or aryloxyimine, thioketo; or $R_3$ and $R_4$ or $Y_1$ and $Y_2$ form a heterocyclic residue selected from the group consisting of aziridinyl, azetidinyl, pyrrolidinyl, piperidinyl, thiazolidinyl, oxazolidinyl, morpholino, piperazinyl, 4-($C_1$-$C_4$) alkylpiperidinyl and N—($C_1$-$C_4$) piperazinyl; and said alkyl, phenyl and naphthyl groups may be substituted with one or more residues selected from the group consisting of ($C_1$-$C_8$) alkyl, halo, nitro, amino, azido and ($C_1$-$C_8$) alkoxyl; and $R_5$ is selected from the group consisting of an optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkynyl, optionally substituted ($C_6$-$C_{20}$) aryl, optionally substituted ($C_3$-$C_{20}$) heteroaryl, optionally substituted ($C_7$-$C_{20}$) arylalkyl, optionally substituted ($C_4$-$C_{20}$) heteroarylalkyl, optionally substituted (C3-$C_{20}$) cycloalkyl, optionally substituted ($C_2$-$C_{20}$) cycloheteroalkyl, N($R_8$)($R_9$); —OR$_{10}$, —SR$_{10}$, —N($R_8$)—C(O)$R_{10}$, —N($R_8$)—C(O)—OR$_{10}$, —N($R_8$)—C(O)—N$R_8R_{10}$, —N($R_8$)—C(S)O$R_{10}$, —N($R_8$)—C(S)—OR$_{10}$, and —N($R_8$)—C(S)—N$R_8R_{10}$.

$R_6$ is selected from the group consisting of, hydrogen, hallo, an optionally substituted or unsubstituted ($C_1$-C10) alkyl, ($C_1$-C10) alkenyl, ($C_6$-C10) aryl.

$R_7$ is selected from the group consisted of hydrogen, an optionally substituted ($C_1$-$C_{10}$) alkyl, optionally substituted (C5-C10) aryl and optionally substituted ($C_1$-$C_{10}$) acyl.

In another embodiment, X is further selected from —N($R_8$) ($R_9$), —N($R_8$)—C(O)$R_{10}$, —N($R_8$)—C(O)—OR$_{10}$, —N($R_8$)—C($R_8$)—C(O)—NR$_8$R$_{10}$, —N($R_8$)—C(S)OR$_{10}$, —N($R_8$)—C(S)—OR$_{10}$, and —N($R_8$)—C(S)—NR$_8$R$_{10}$.

In another embodiment, a pharmaceutical composition is provided comprising the aforedescribed compound and a pharmaceutically-acceptable carrier.

In yet another embodiment, a composition for administration to a mammalian subject is provided. The composition comprises a plurality of particles which comprise the compound of formula I, wherein the average size of the particles is no greater than about 500 nm, and preferably no greater than about 200 nm.

In yet another embodiment, a method of treating a disease or condition characterized by undesirable cellular proliferation or hyperproliferation is provided. In this method, a composition containing the compound described above is administered to a subject in need of such treatment.

These and other advantages of the present invention are described more fully below.

DETAILED DESCRIPTION OF THE INVENTION

The invention provides pure and isolated, reduced forms of analogs of benzoquinone imine-containing ansamycin and its acylation or alkylation derivatives therefor. The present invention also provided methods for the use of these compounds in the treatment of diseases or conditions characterized by undesired cellular hyperproliferation, such as cancer, as well as other conditions and disorders associated with Hsp90 activity or in which Hsp90 plays a role in the cells involved in causing the disorder. The present invention provided reduced analogs of benzoquinone ansamycins where the benzoqionone oxime is reduced to a hydroquinone amine, and preferably acylized to form amide hydroquinone, further methylation. The present invention relates to compounds of the formula I as well as pharmaceutically-acceptable salts and prodrugs thereof, hereinafter referred to as the active compounds derivatized from ansamycins.

In a first aspect, the invention comprises compounds of formula (I)

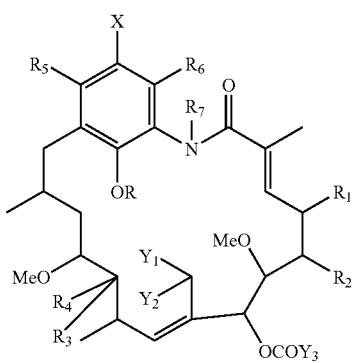

(I)

wherein

X is selected from the group consisting of —N($R_8$)($R_9$), —N($R_8$)—C(O)$R_{10}$, —N($R_8$)—C(O)—OR$_{10}$, —N($R_8$)—SO$_2$R10, —N($R_8$)—C(O)—NR$_8$R$_{10}$, —N($R_8$)—C(S)OR$_{10}$, —N($R_8$)—C(S)—OR$_{10}$, and —N($R_8$)—C(S)—NR$_8$R$_{10}$; wherein $R_8$ and $R_9$ are independently selected from the group consisting of H, optionally substituted ($C_1$-$C_{20}$) alkyl, optionally substituted ($C_2$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkynyl, optionally substituted aryl, optionally substituted heteroaryl, optionally substituted arylalkyl, optionally substituted heteroarylalkyl, optionally substituted cycloalkyl, and optionally substituted cycloheteroalkyl; $R_8$ is selected from the group consisting of H, optionally substituted ($C_1$-$C_6$) alkyl, optionally substituted ($C_5$-$C_8$) aryl, and an optionally substituted ($C_5$-$C_8$) heteroaryl, or together with $R_9$ form an optionally substituted 4-7 membered heterocyclic or carbocyclic ring;

$R_{10}$ is selected from the group consisting of hydrogen, an optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkynyl, optionally substituted ($C_6$-$C_{20}$) aryl, optionally substituted ($C_3$-$C_{20}$) heteroaryl, optionally substituted ($C_7$-$C_{20}$) arylalkyl, optionally substituted ($C_4$-$C_{20}$) heteroarylalkyl, optionally substituted ($C_3$-$C_{20}$) cycloalkyl, and an optionally substituted ($C_2$-$C_{20}$) cycloheteroalkyl;

R represents, hydrogen, substituted or unsubstituted ($C_1$-$C_6$) alkyl or ($C_1$-$C_6$) alkenyl or ($C_6$-$C_{10}$) aryl or OCOR10;

$R_1$ and $R_2$ are each a hydrogen or $R_1$ and $R_2$ together form a single bond;

$R_3$, $R_4$, $Y_1$, $Y_2$, $Y_3$ are independently selected from the group consisting H, halo, —OH, O-alkyl, O-acetyl, —O-aryl, OC(O) $R_{10}$, —SO$_2$—$R_{10}$, and —NHR$_{10}$, or together form oxo (=O), or hydroxylamino alkoxyimine or aryloxyimine, thioketo; or $R_3$ and $R_4$ or $Y_1$ and $Y_2$ form a heterocyclic residue selected from the group consisting of aziridinyl, azetidinyl, pyrrolidinyl, piperidinyl, thiazolidinyl, oxazolidinyl, morpholino, piperazinyl, 4-($C_1$-$C_4$) alkylpiperidinyl and N—($C_1$-$C_4$) piperazinyl; and said alkyl, phenyl and naphthyl groups may be substituted with one or more residues selected from the group consisting of ($C_1$-$C_8$) alkyl, halo, nitro, amino, azido and ($C_1$-$C_8$) alkoxyl; and $R_5$ is selected from the group consisting of an optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkynyl, optionally substituted ($C_6$-$C_{20}$) aryl, optionally substituted ($C_3$-$C_{20}$) heteroaryl, optionally substituted ($C_7$-$C_{20}$) arylalkyl, optionally substituted ($C_4$-$C_{20}$) heteroarylalkyl, optionally substituted (C3-$C_{20}$) cycloalkyl, optionally substituted ($C_2$-$C_{20}$) cycloheteroalkyl, N($R_8$)($R_9$); —OR$_{10}$, —SR$_{10}$, —N($R_8$)—C(O)R$_{10}$, —N($R_8$)—C(O)—OR$_{10}$, —N($R_8$)—C(O)—NR$_8$R$_{10}$, —N($R_8$)—C(S)OR$_{10}$, —N($R_8$)—C(S)—OR$_{10}$, and —N($R_8$)—C(S)—NR$_8$R$_{10}$.

$R_6$ is selected from the group consisting of, hydrogen, hallo, an optionally substituted or unsubstituted ($C_1$-C10) alkyl, ($C_1$-C10) alkenyl, ($C_6$-C10) aryl.

$R_7$ is selected from the group consisted of hydrogen, an optionally substituted ($C_1$-C10) alkyl, optionally substituted (C5-C10) aryl and optionally substituted ($C_1$-C10) acyl.

In another embodiment, X is further selected from —N($R_8$) ($R_9$), —N($R_8$)—C(O)$R_{10}$, —N($R_8$)—C(O)—OR$_{10}$, —N($R_8$)—C(O)—NR$_8$R$_{10}$, —N($R_8$)—SO$_2$R10, —N($R_8$)—C(S)OR$_{10}$, —N($R_8$)—C(S) —OR$_{10}$, and —N($R_8$)—C(S)—NR$_8$R$_{10}$.

The following definitions refer to the various terms used above and throughout the disclosure.

The term "halo" refers to fluoro, chloro, bromo or iodo.

The term "($C_1$-$C_{20}$) alkyl" refers to an alkyl, substituted straight or branched chain alkyl or alkylenyl group, having from 1-20 carbon atoms. In view of availability of alkylating reactants, the alkyl group has preferably 1-10 carbon atoms. Illustrative of the alkyl group include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl and 6-propylundecyl groups.

The term "($C_2$-$C_{20}$) alkenyl" represents an alkenyl group, having from 2 to 20 carbon atoms, and may be a straight or branched chain group, preferably, natural or unnatural fatty acid. It may have 1 or more, preferably from 2 to 6, double bonds. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 1-octenyl, 8-nonenyl, 1-nonenyl, 1-decenyl, 9-decenyl, 8-tridecenyl, cis-8-pentadecenyl, trans-8-pentadecenyl, 8-heptadecenyl, 8-heptadecenyl, 8,11-heptadecadienyl, 8,11,14-heptadecatrienyl, 4,7,11,14-nonadecatetraenyl and 2,6-dimethyl-8-(2,6,6-trimethyl-1-cyclohexen-1-yl)-1,3,5,7-nonatetraen-1-yl, cis-10-nonadecaenyl, 10,13-nonadecadienyl, cis-7,10,13-nonadecatrienyl, 5,8,11,14-nonadecatetraenyl, nonadecapentaenyl.

The term "($C_1$-$C_8$) alkoxy" refers to an alkoxy group with one to eight carbon alkyl groups, and the alkyl moiety thereof generally corresponds to the $C_1$-$C_{20}$ alkyl groups described above and can be selected therefrom. Examples of alkoxy groups are those derived from straight or branched chain lower alkyl groups with 1-8 carbon atoms, and include, for example, methoxy, ethoxy n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "($C_3$-$C_{20}$) aryl" refers to an aromatic or heteroaromatic ring, including by way of example, phenyl, naphthyl, furanyl, imidazolyl and thionyl. The aryl ring can be substituted with substituents selected from the group consisting of halo, $C_1$-$C_6$ alkyl or $C_1$-$C_6$ alkoxy, or alkyl amino. Examples include 4-chlorophenyl, 2-fluorophenyl, 4-fluorophenyl, 3-fluorophenyl, 4-methylphenyl, 4-ditrifluorohenyl, 2-ethylphenyl, 3-n-propylphenyl, 4-isopropyl-phenyl, 4-n-butylphenyl, 4-t-butylphenyl, 4-sec-butylphenyl, 4-dimethylaminophenyl, 3,4-dimethylphenyl, 4-methoxyphenyl, 4-ethoxyphenyl, 4-isopropoxyphenyl, 3-isobutoxyphenyl, 4-t-butoxyphenyl, 4-nitrophenyl, 2-furan, 2-pyridyl, 3-pyridyl, 2-thiophenyl, 3-thiophenyl, 1-naphthyl, 2-naphthyl, 2-indolyl, and the like, and the aryl moiety of aryl and arylcarbamoyl have the same meaning.

Examples of the heterocyclic group include alicyclic heterocyclic groups, aromatic heterocyclic groups, and the like, such as pyridonyl, pyrrolidonyl, uracilyl, dioxolnyl, pyrrolyl, tetrazolyl, pyrrolidinyl, thienyl, morpholino, thiomorpholino, piperazinyl, pyrazolidinyl, piperidino, pyridyl, hompiperazinyl, pyrazolyl, pyrazinyl, indolyl, isoindolyl, furyl, piperidyl, quinolyl, phthalazinyl, imidazolidinyl, imidazolinyl, pyrimidinyl, and the like. The heterocylic group moiety in the carbonyl bound to a heterocyclic ring has the same meaning as defined above, and examples of the entire group containing carbonyl include furoyl, thenoyl, nicotinoyl, isonicotinoyl, and the like. Examples of the nitrogen containing heterocyclic group formed by $R_8$ and $R_9$ with the adjoining N and the nitrogen containing heterocyclic group formed by $R_8$ and $R_9$ with the adjoining N (said heterocyclic group may further contain O, S or other N) include pyrrolidyl, morpholino, thiomorpholino, piperazinyl, pyrazolidinyl, pyrazolinyl, piperidino, homopiperazinyl, indolinyl, isoindolinyl, perhydroazepinyl, perhydroazocinyl, indolyl, isoindolyl, and the like.

The term "$OR_{10}$, $SR_{10}$ and $NR_8R_9$" refers to the allyl groups substituted with oxygen, sulfur and nitrogen. Preferred examples of the alkyl group substituted with oxygen, sulfur or nitrogen include methoxymethyl, ethoxymethyl, propoxymethyl, n-butoxymethyl, 2-methoxyethyl, 2-ethoxyethyl, 2-propoxyethyl, 3-methoxypropyl, 3-ethoxypropyl, 3-propoxypropyl, 4-methoxybutyl, 4-propoxybutyl, dimethoxymethyl, 2,2-dimethoxyethyl, diethoxymethyl, 2,2-diethoxyethyl, dipropoxymethyl and 2,2-dipropoxyethyl groups. Preferred examples of $(CH_2)_n SR_5$ are methylthiomethyl, ethylthiomethyl, propylthiomethyl, n-butylthiomethyl, 2-methylthioethyl, 2-ethylthiolethyl, 2-propylthiolethyl, 3-methylthiopropyl, 3-ethylthiopropyl, 3-propylthiopropyl, 4-methylthiobutyl, and 4-propylthiobutyl groups. Preferred examples of $(CH_2)_n NR_5R_6$ are aminomethyl, dimethylaminomethyl, (N-actyl)methylaminomethyl, diethylaminomethyl, dipropylaminomethyl, dibutylaminomethyl, dimethylaminoethyl, diethylaminoethyl, dipropylaminoethyl, and dibutylaminoethyl groups.

The term "$COR_{10}$" refers to carboxylic acid, ester, or amide, wherein $R_{10}$ generally correspond to the $C_1$-$C_{20}$ alkyl groups discussed above and can be selected therefrom. Preferred examples of the alkylamino group are those derived from hydrogen, and straight or branched chain lower alkyl groups with 1-6 carbon atoms, such as methyl, ethyl, propyl, butyl, pentyl and hexyl groups.

The term "—N($R_8$)—C(O)$R_{10}$, —N($R_8$)—C(O)—$OR_{10}$, —N($R_8$)—C(O)—$NR_8R_{10}$, —N($R_8$)—$SO_2R10$, —N($R_8$)—C(S)$OR_{10}$, —N($R_8$)—C(S)—$OR_{10}$, —N($R_8$)—C(S)—$NR_8R_{10}$" refers to compounds wherein $R_8$ and $R_{10}$ are the same or different, and each represents hydrogen, hydroxyl, alkyl, cycloalkyl, alkoxy, aryl, heterocyclic group, alkanoyl, or $NR_8R_{10}$ represents a substituted or unsubstituted aryl, substituted or unsubstituted pyridyl, substituted or unsubstituted pyridonyl, substituted or unsubstituted pyrrolidonyl, substituted or unsubstituted uracilyl, substituted or unsubstituted piperidyl, substituted or unsubstituted piperidino, substituted or unsubstituted pyrolidinyl, substituted or unsubstituted morpholino, substituted or unsubstituted morpholinyl, substituted or unsubstituted piperazinyl, substituted or unsubstituted thiomorpholino, substituted or unsubstituted dioxolanyl, cyclic imido (a group formed by removing hydrogen bound to an imido N atom).

The term "heteroaryl" refers to optionally substituted aromatic ring systems containing from about five to about 20 skeletal ring atoms and having one or more heteroatoms such as, for example, oxygen, nitrogen, sulfur, and phosphorus. The term 15 heteroaryl also includes optionally substituted aromatic ring systems having from 5 to about 12 skeletal ring atoms, as well as those having from 5 to about 10 skeletal ring atoms. The term heteroaryl may include five- or six-membered heterocyclic rings, polycyclic heteroaromatic ring systems and polyheteroaromatic ring systems where the ring system has two, three or four rings. The terms heterocyclic, polycyclic heteroaromatic and polyheteroaromatic include ring systems containing optionally substituted heteroaromatic rings having more than one heteroatom as described above (e.g. a six membered ring with two nitrogens), including polyheterocyclic ring systems of from two to four rings. The term heteroaryl includes ring systems such as, for example, furanyl, benzofuranyl, chromenyl, pyridyl, pyrrolyl, indolyl, quinolinyl, N-alkyl pyrrolyl, pyridyl-N-oxide, pyrimidoyl, pyrazinyl, imidazolyl, pyrazolyl, oxazolyl, benzothiophenyl, purinyl, indolizinyl, thienyl and the like.

The term "acyl" includes alkyl, aryl, heteroaryl, arylalkyl or heteroarylalkyl substituents attached to a compound via a carbonyl functionality (e.g., —CO-alkyl, —CO-aryl, —CO-arylalkyl or —CO-heteroarylalkyl, etc.).

The term "Pharmaceutically acceptable salts" of the compounds of the invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, gluconic, lactic, salicylic, succinic, toluene-p sulfonic, tartaric, acetic, citric, methanesulfonic, formic, benzoic, malonic, naphthalene-2-sulfonic, benzenesulfonic, 1,2 ethanesulfonic acid (edisylate), galactosyl-d-gluconic acid, and the like. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g. sodium), alkaline earth metal (e.g. magnesium), ammonium and N—(C. sub. $1$-$C_4$ alkyl)$_4{}^+$ salts, and the like. Illustrative examples of some of these include sodium hydroxide, potassium hydroxide, choline hydroxide, sodium carbonate, and the like.

Preferably, when X represents substituted or unsubstituted ($C_1$-$C_6$) alkyl or ($C_1$-$C_6$) alkenyl or ($C_6$-$C_{10}$) aryl, —N($R_8$)—C(O)$R_{10}$, N($R_8$)—C(O)—OR$_{10}$, —N($R_8$)—SO$_2$R$_{10}$, or —N($R_8$)—C(O)—NR$_8$R$_{10}$, wherein $R_8$ and $R_9$ are each independently selected from the group consisting of hydrogen, ($C_1$-$C_8$) alkyl, ($C_3$-$C_8$) cycloalkyl, ($C_2$-$C_8$) alkenyl and ($C_2$-$C_8$) alkynyl; wherein said alkyl, alkenyl and alkynyl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, and ($C_2$-$C_6$) heterocycloalkyl and ($C_2$-$C_6$) heterocycloaryl groups selected from the group comprising imidizaloly, furyl, tetrahydrofuryl; and if comprising more than two carbon atoms may be branched, cyclic or unbranched or combinations of branched, cyclic and unbranched groups; or $R_8$ and $R_9$ together with the nitrogen to which they are attached, form a heterocyclic residue selected from the group consisting of aziridinyl, azetidinyl and pyrrolidinyl; NR$_8$R$_{10}$ is selected from the group consisting of 1-piperidinamine, 4-morpholinamine, methylamine, ethylamine, propylamine, butylamine, pentylamine, hexylamine, heptylamine, octylamine, allylamine, β-hydroxyethylamine, β-chloroethylamine, β-glycoxyethylamine, aminobutylamine, adamantylmethylamine, cyclopropylamine, cyclopentylamine, cyclohexylamine, cycloheptylamine, cyclooctylamine, benzylamine, phenethylamine, ethyleneamine, pyrrolidine, piperidine, dimethylamine, aminoethylamine, diglycolamine, β-morpholinoethylamine, β-piperidinoethylamine, picolylamine, β-pyrrolidinoethylamine, β-pyridinylethylamine, β-methoxyethylamine, and β-N-methylaminoethylamine;

R represents, hydrogen, substituted or unsubstituted ($C_1$-$C_6$) alkyl or ($C_1$-$C_6$) alkenyl or ($C_6$-$C_{10}$) aryl.

Preferably, the compounds of the invention may be compounds of formula (I) wherein A: X is NR$_8$N$_9$; R represents, hydrogen, substituted or unsubstituted ($C_1$-$C_6$) alkyl or ($C_1$-$C_6$) alkenyl or ($C_6$-$C_{10}$) aryl;

$R_1$ and $R_2$ together form a single bond; $R_3$, $R_6$, $R_7$, $Y_1$, $Y_2$ and $Y_3$ are each hydrogen; $R_4$ is fluoro, or OR$_{10}$, $R_5$ is OR$_{10}$ or NR$_8$R$_9$; when $R_5$ is R$_{10}$O, R$_{10}$ is hydrogen or ($C_1$-$C_8$)alkyl; when $R_5$ is R$_8$R$_9$N, R$_8$ and R$_9$ is selected from hydrogen, ($C_1$-$C_8$) alkyl, ($C_1$-$C_8$) alkoxy, ($C_3$-$C_8$) cycloalkyl, ($C_2$-$C_8$) alkenyl and ($C_2$-$C_8$) alkynyl; wherein said alkyl, alkoxy, alkenyl and alkynyl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, ($C_2$-$C_6$) heterocycloalkyl and ($C_2$-$C_6$) heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, ($C_1$-$C_8$) alkylthio, substituted or unsubstituted amino, hydroxyl, ($C_1$-$C_8$) alkoxyl, carboxyl, amidino and acylamino;

when N($R_8$)($R_9$) is selected from —OR$_{10}$, —SR$_{10}$, —N($R_8$)—C(O)R$_{10}$, —N($R_8$)—C(O)—OR$_{10}$, —N($R_8$)—C(O)—NR$_8$R$_{10}$, —N($R_8$)—C(S)OR$_{10}$, —N($R_8$)—C(S)—OR$_{10}$, —N($R_8$)—C(S)—NR$_8$R$_{10}$; wherein $R_8$ and $R_{10}$ are selected from the group consisting of H, optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

B: X is N($R_8$)—C(O)R$_{10}$, wherein $R_8$ and $R_{10}$ are each independently selected from the group consisting of hydrogen, ($C_1$-$C_8$) alkyl, ($C_3$-$C_8$) cycloalkyl, ($C_2$-$C_8$) alkenyl and ($C_2$-$C_8$) alkynyl, (C4-C10)aryl; wherein said alkyl, alkenyl, alkynyl and aryl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, and ($C_2$-$C_6$) heterocycloalkyl and ($C_2$-$C_6$) heterocycloaryl groups selected from the group comprising imidizaloly, furyl, tetrahydrofuryl; and if comprising more than two carbon atoms may be branched, cyclic or unbranched or combinations of branched, cyclic and unbranched groups;

R represents, hydrogen, substituted or unsubstituted ($C_1$-$C_6$) alkyl or ($C_1$-$C_6$) alkenyl or ($C_6$-$C_{10}$) aryl;

$R_1$ and $R_2$ together form a single bond; $R_3$, $R_6$, $R_7$, $Y_1$, $Y_2$ and $Y_3$ are each hydrogen; $R_4$ is fluoro, or OR$_{10}$, $R_5$ is OR$_{10}$ or NR$_8$R$_9$; When $R_5$ is R$_{10}$O, R$_{10}$ is hydrogen or ($C_1$-$C_8$)alkyl; when $R_5$ is R$_8$R$_9$N, R$_8$ and R$_9$ is selected from hydrogen, ($C_1$-$C_8$) alkyl, ($C_1$-$C_8$) alkoxy, ($C_3$-$C_8$) cycloalkyl, ($C_2$-$C_8$) alkenyl and ($C_2$-$C_8$) alkynyl; wherein said alkyl, alkoxy, alkenyl and alkynyl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, ($C_2$-$C_6$) heterocycloalkyl and ($C_2$-$C_6$) heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, ($C_1$-$C_8$) alkylthio, substituted or unsubstituted amino, hydroxyl, ($C_1$-$C_8$) alkoxyl, carboxyl, amidino and acylamino;

when $N(R_8)(R_9)$ is selected from —$OR_{10}$, —$SR_{10}$, —$N(R_8)$—$C(O)R_{10}$, —$N(R_8)$—$C(O)$—$OR_{10}$, —$N(R_8)$—$C(O)$—$NR_8R_{10}$, —$N(R_8)$—$C(S)OR_{10}$, —$N(R_8)$—$C(S)$—$OR_{10}$, —$N(R_8)$—$C(S)$—$NR_8R_{10}$; wherein $R_8$ and $R_{10}$ are selected from the group consisting of H, optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

C: X is $N(R_8)$—$C(O)OR_{10}$, wherein $R_8$ and $R_{10}$ are each independently selected from the group consisting of hydrogen, ($C_1$-$C_8$) alkyl, ($C_3$-$C_8$) cycloalkyl, ($C_2$-$C_8$) alkenyl and ($C_2$-$C_8$) alkynyl, (C4-C10)aryl; wherein said alkyl, alkenyl, alkynyl and aryl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, and ($C_2$-$C_6$) heterocycloalkyl and ($C_2$-$C_6$) heterocycloaryl groups selected from the group comprising imidizaloly, furyl, tetrahydrofuryl; and if comprising more than two carbon atoms may be branched, cyclic or unbranched or combinations of branched, cyclic and unbranched groups;

R represents, hydrogen, substituted or unsubstituted ($C_1$-$C_6$) alkyl or ($C_1$-$C_6$) alkenyl or ($C_6$-$C_{10}$) aryl;

$R_1$ and $R_2$ together form a single bond; $R_3$, $R_6$, $R_7$, $Y_1$, $Y_2$ and $Y_3$ are each hydrogen; $R_4$ is fluoro, or $OR_{10}$, $R_5$ is $OR_{10}$ or $NR_8R_9$; When $R_5$ is $R_{10}O$, $R_{10}$ is hydrogen or ($C_1$-$C_8$)alkyl; when $R_5$ is $R_8R_9N$, $R_8$ and R9 is selected from hydrogen, ($C_1$-$C_8$) alkyl, ($C_1$-$C_8$) alkoxy, ($C_3$-$C_8$) cycloalkyl, ($C_2$-$C_8$) alkenyl and ($C_2$-$C_8$) alkynyl; wherein said alkyl, alkoxy, alkenyl and alkynyl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, ($C_2$-$C_6$) heterocycloalkyl and ($C_2$-$C_6$) heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, ($C_1$-$C_8$) alkylthio, substituted or unsubstituted amino, hydroxyl, ($C_1$-$C_8$) alkoxyl, carboxyl, amidino and acylamino;

when $N(R_8)(R_9)$ is selected from —$OR_{10}$, —$SR_{10}$, —$N(R_8)$—$C(O)R_{10}$, —$N(R_8)$—$C(O)$—$OR_{10}$, —$N(R_8)$—$C(O)$—$NR_8R_{10}$, —$N(R_8)$—$C(S)OR_{10}$, —$N(R_8)$—$C(S)$—$OR_{10}$, —$N(R_8)$—$C(S)$—$NR_8R_{10}$; wherein $R_8$ and $R_{10}$ are selected from the group consisting of H, optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

D: X is $N(R_8)$—$C(O)$—$NR_8R_{10}$, wherein $R_8$ and $R_{10}$ are each independently selected from the group consisting of hydrogen, ($C_1$-$C_8$) alkyl, ($C_3$-$C_8$) cycloalkyl, ($C_2$-$C_8$) alkenyl and ($C_2$-$C_8$) alkynyl, (C4-C10)aryl; wherein said alkyl, alkenyl, alkynyl and aryl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, and ($C_2$-$C_6$) heterocycloalkyl and ($C_2$-$C_6$) heterocycloaryl groups selected from the group comprising imidizaloly, furyl, tetrahydrofuryl; and if comprising more than two carbon atoms may be branched, cyclic or unbranched or combinations of branched, cyclic and unbranched groups;

R represents, hydrogen, substituted or unsubstituted ($C_1$-$C_6$) alkyl or ($C_1$-$C_6$) alkenyl or ($C_6$-$C_{10}$) aryl;

$R_1$ and $R_2$ together form a single bond; $R_3$, $R_6$, $R_7$, $Y_1$, $Y_2$ and $Y_3$ are each hydrogen; $R_4$ is fluoro, or $OR_{10}$, $R_5$ is $OR_{10}$ or $NR_8R_9$; When $R_5$ is $R_{10}O$, $R_{10}$ is hydrogen or ($C_1$-$C_8$)alkyl; when $R_5$ is $R_8R_9N$, $R_8$ and $R_9$ is selected from hydrogen, ($C_1$-$C_8$) alkyl, ($C_1$-$C_8$) alkoxy, ($C_3$-$C_8$) cycloalkyl, ($C_2$-$C_8$) alkenyl and ($C_2$-$C_8$) alkynyl; wherein said alkyl, alkoxy, alkenyl and alkynyl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, ($C_2$-$C_6$) heterocycloalkyl and ($C_2$-$C_6$) heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, ($C_1$-$C_8$) alkylthio, substituted or unsubstituted amino, hydroxyl, ($C_1$-$C_8$) alkoxyl, carboxyl, amidino and acylamino;

when $N(R_8)(R_9)$ is selected from —$OR_{10}$, —$SR_{10}$, —$N(R_8)$—$C(O)R_{10}$, —$N(R_8)$—$C(O)$—$OR_{10}$, —$N(R_8)$—$C(O)$—$NR_8R_{10}$, —$N(R_8)$—$C(S)OR_{10}$, —$N(R_8)$—$C(S)$—$OR_{10}$, —$N(R_8)$—$C(S)$—$NR_8R_{10}$; wherein $R_8$ and $R_{10}$ are selected from the group consisting of H, optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

E: X is $-N(R_8)-SO_2R_{10}$, wherein $R_8$ and $R_{10}$ are each independently selected from the group consisting of hydrogen, $(C_1-C_8)$ alkyl, $(C_3-C_8)$ cycloalkyl, $(C_2-C_8)$ alkenyl and $(C_2-C_8)$ alkynyl, (C4-C10)aryl; wherein said alkyl, alkenyl, alkynyl and aryl are optionally substituted wherein said substituents are selected from the group consisting of halo, cyano, mercapto, $(C_1-C_8)$ alkylthio, optionally substituted amino, hydroxyl, $(C_1-C_8)$ alkoxyl, carboxyl, amidino, acylamino, and $(C_2-C_6)$ heterocycloalkyl and $(C_2-C_6)$ heterocycloaryl groups selected from the group comprising imidizaloly, furyl, tetrahydrofuryl; and if comprising more than two carbon atoms may be branched, cyclic or unbranched or combinations of branched, cyclic and unbranched groups;

R represents, hydrogen, substituted or unsubstituted $(C_1-C_6)$ alkyl or $(C_1-C_6)$ alkenyl or $(C_6-C_{10})$ aryl;

$R_1$ and $R_2$ together form a single bond; $R_3$, $R_6$, $R_7$, $Y_1$, $Y_2$ and $Y_3$ are each hydrogen; $R_4$ is fluoro, or $OR_{10}$, $R_5$ is $OR_{10}$ or $NR_8R_9$; When $R_5$ is $R_{10}O$, $R_{10}$ is hydrogen or $(C_1-C_8)$alkyl;

when $R_5$ is $R_8R_9N$, $R_8$ and $R_9$ is selected from hydrogen, $(C_1-C_8)$ alkyl, $(C_1-C_8)$ alkoxy, $(C_3-C_8)$ cycloalkyl, $(C_2-C_8)$ alkenyl and $(C_2-C_8)$ alkynyl; wherein said alkyl, alkoxy, alkenyl and alkynyl are optionally substituted wherein said substituents are selected from the group consisting of halo, cyano, mercapto, $(C_1-C_8)$ alkylthio, optionally substituted amino, hydroxyl, $(C_1-C_8)$ alkoxyl, carboxyl, amidino, acylamino, $(C_2-C_6)$ heterocycloalkyl and $(C_2-C_6)$ heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, $(C_1-C_8)$ alkylthio, substituted or unsubstituted amino, hydroxyl, $(C_1-C_8)$ alkoxyl, carboxyl, amidino and acylamino;

when $N(R_8)(R_9)$ is selected from $-OR_{10}$, $-SR_{10}$, $-N(R_8)-C(O)R_{10}$, $-N(R_8)-C(O)-OR_{10}$, $N(R_8)-C(O)-NR_8R_{10}$, $-N(R_8)-C(S)OR_{10}$, $-N(R_8)-C(S)-OR_{10}$, $-N(R_8)-C(S)-NR_8R_{10}$; wherein $R_8$ and $R_{10}$ are selected from the group consisting of H, optionally substituted $(C_1-C_{20})$ alkyl, optionally substituted $(C_1-C_{20})$ heteroalkyl, optionally substituted $(C_2-C_{20})$ alkenyl, optionally substituted $(C_2-C_{20})$ heteroalkenyl, optionally substituted $(C_2-C_{20})$ alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

F: X is $NR_8N_9$;

$R_1$, $R_2$, $R_3$, $R_6$, $R_7$, $Y_1$, $Y_2$ and $Y_3$ are each hydrogen; $R_4$ is fluoro, or $OR_{10}$, $R_5$ is $OR_{10}$ or $NR_8R_9$; When $R_5$ is $R_{10}O$, $R_{10}$ is hydrogen or $(C_1-C_8)$alkyl; when $R_5$ is $R_8R_9N$, $R_8$ and $R_9$ is selected from hydrogen, $(C_1-C_8)$ alkyl, $(C_1-C_8)$ alkoxy, $(C_3-C_8)$ cycloalkyl, $(C_2-C_8)$ alkenyl and $(C_2-C_8)$ alkynyl; wherein said alkyl, alkoxy, alkenyl and alkynyl are optionally substituted wherein said substituents are selected from the group consisting of halo, cyano, mercapto, $(C_1-C_8)$ alkylthio, optionally substituted amino, hydroxyl, $(C_1-C_8)$ alkoxyl, carboxyl, amidino, acylamino, $(C_2-C_6)$ heterocycloalkyl and $(C_2-C_6)$ heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, $(C_1-C_8)$ alkylthio, substituted or unsubstituted amino, hydroxyl, $(C_1-C_8)$ alkoxyl, carboxyl, amidino and acylamino;

when $N(R_8)(R_9)$ is selected from $-OR_{10}$, $-SR_{10}$, $-N(R_8)-C(O)R_{10}$, $-N(R_8)-C(O)-OR_{10}$, $-N(R_8)-C(O)-NR_8R_{10}$, $-N(R_8)-C(S)OR_{10}$, $-N(R_8)-C(S)-OR_{10}$, $-N(R_8)-C(S)-NR_8R_{10}$; wherein $R_8$ and $R_{10}$ are selected from the group consisting of H, optionally substituted $(C_1-C_{20})$ alkyl, optionally substituted $(C_1-C_{20})$ heteroalkyl, optionally substituted $(C_2-C_{20})$ alkenyl, optionally substituted $(C_2-C_{20})$ heteroalkenyl, optionally substituted $(C_2-C_{20})$ alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

G: X is $N(R_8)-C(O)R_{10}$, wherein $R_8$ and $R_{10}$ are each independently selected from the group consisting of hydrogen, $(C_1-C_8)$ alkyl, $(C_3-C_8)$ cycloalkyl, $(C_2-C_8)$ alkenyl and $(C_2-C_8)$ alkynyl, (C4-C10)aryl; wherein said alkyl, alkenyl, alkynyl and aryl are optionally substituted wherein said substituents are selected from the group consisting of halo, cyano, mercapto, $(C_1-C_8)$ alkylthio, optionally substituted amino, hydroxyl, $(C_1-C_8)$ alkoxyl, carboxyl, amidino, acylamino, and $(C_2-C_6)$ heterocycloalkyl and $(C_2-C_6)$ heterocycloaryl groups selected from the group comprising imidizaloly, furyl, tetrahydrofuryl; and if comprising more than two carbon atoms may be branched, cyclic or unbranched or combinations of branched, cyclic and unbranched groups;

R represents, hydrogen, substituted or unsubstituted $(C_1-C_6)$ alkyl or $(C_1-C_6)$ alkenyl or $(C_6-C_{10})$ aryl;

$R_1$, $R_2$, $R_3$, $R_6$, $R_7$, $Y_1$, $Y_2$ and $Y_3$ are each hydrogen; $R_4$ is fluoro, or $OR_{10}$, $R_5$ is $OR_{10}$ or $NR_8R_9$; When $R_5$ is $R_{10}O$, $R_{10}$ is hydrogen or $(C_1-C_8)$alkyl; when $R_5$ is $R_8R_9N$, $R_8$ and R9 is selected from hydrogen, $(C_1-C_8)$ alkyl, $(C_1-C_8)$ alkoxy, $(C_3-C_8)$ cycloalkyl, $(C_2-C_8)$ alkenyl and $(C_2-C_8)$ alkynyl; wherein said alkyl, alkoxy, alkenyl and alkynyl are optionally substituted wherein said substituents are selected from the group consisting of halo, cyano, mercapto, $(C_1-C_8)$ alkylthio, optionally substituted amino, hydroxyl, $(C_1-C_8)$ alkoxyl, carboxyl, amidino, acylamino, $(C_2-C_6)$ heterocycloalkyl and $(C_2-C_6)$ heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, $(C_1-C_8)$ alkylthio, substituted or unsubstituted amino, hydroxyl, $(C_1-C_8)$ alkoxyl, carboxyl, amidino and acylamino;

when $N(R_8)(R_9)$ is selected from $-OR_{10}$, $-SR_{10}$, $-N(R_8)-C(O)R_{10}$, $-N(R_8)-C(O)-OR_{10}$, $-N(R_8)-C$ (O)—$NR_8R_{10}$, —$N(R_8)$—C(S)$OR_{10}$, —$N(R_8)$—C(S)—$OR_{10}$, —$N(R_8)$—C(S)—$NR_8R_{10}$; wherein $R_8$ and $R_{10}$ are selected from the group consisting of H, optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

H: X is $N(R_8)$—C(O)$OR_{10}$, wherein $R_8$ and $R_{10}$ are each independently selected from the group consisting of hydrogen, ($C_1$-$C_8$) alkyl, ($C_3$-$C_8$) cycloalkyl, ($C_2$-$C_8$) alkenyl and ($C_2$-$C_8$) alkynyl, (C4-C10)aryl; wherein said alkyl, alkenyl, alkynyl and aryl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, and ($C_2$-$C_6$) heterocycloalkyl and ($C_2$-$C_6$) heterocycloaryl groups selected from the group comprising imidizaloly, furyl, tetrahydrofuryl; and if comprising more than two carbon atoms may be branched, cyclic or unbranched or combinations of branched, cyclic and unbranched groups;

R represents, hydrogen, substituted or unsubstituted ($C_1$-$C_6$) alkyl or ($C_1$-$C_6$) alkenyl or ($C_6$-$C_{10}$) aryl;

$R_1$, $R_2$, $R_3$, $R_6$, $R_7$, $Y_1$, $Y_2$ and $Y_3$ are each hydrogen; $R_4$ is fluoro, or $OR_{10}$, $R_5$ is $OR_{10}$ or $NR_8R_9$; When $R_5$ is $R_{10}O$, $R_{10}$ is hydrogen or ($C_1$-$C_8$)alkyl; when $R_5$ is $R_8R_9N$, $R_8$ and $R_9$ is selected from hydrogen, ($C_1$-$C_8$) alkyl, ($C_1$-$C_8$) alkoxy, ($C_3$-$C_8$) cycloalkyl, ($C_2$-$C_8$) alkenyl and ($C_2$-$C_8$) alkynyl; wherein said alkyl, alkoxy, alkenyl and alkynyl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, ($C_2$-$C_6$) heterocycloalkyl and ($C_2$-$C_6$) heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, ($C_1$-$C_8$) alkylthio, substituted or unsubstituted amino, hydroxyl, ($C_1$-$C_8$) alkoxyl, carboxyl, amidino and acylamino;

when $N(R_8)(R_9)$ is selected from —$OR_{10}$, —$SR_{10}$, —$N(R_8)$—C(O)$R_{10}$, —$N(R_8)$—C(O)—$OR_{10}$, $N(R_8)$—C(O)—$NR_8R_{10}$, —$N(R_8)$—C(S)$OR_{10}$, —$N(R_8)$—C(S)—$OR_{10}$, —$N(R_8)$—C(S)—$NR_8R_{10}$; wherein $R_8$ and $R_{10}$ are selected from the group consisting of H, optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

I: X is $N(R_8)$—C(O)—$NR_8R_{10}$, wherein $R_8$ and $R_{10}$ are each independently selected from the group consisting of hydrogen, ($C_1$-$C_8$) alkyl, ($C_3$-$C_8$) cycloalkyl, ($C_2$-$C_8$) alkenyl and ($C_2$-$C_8$) alkynyl, (C4-C10)aryl; wherein said alkyl, alkenyl, alkynyl and aryl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, and ($C_2$-$C_6$) heterocycloalkyl and ($C_2$-$C_6$) heterocycloaryl groups selected from the group comprising imidizaloly, furyl, tetrahydrofuryl; and if comprising more than two carbon atoms may be branched, cyclic or unbranched or combinations of branched, cyclic and unbranched groups;

R represents, hydrogen, substituted or unsubstituted ($C_1$-$C_6$) alkyl or ($C_1$-$C_6$) alkenyl or ($C_6$-$C_{10}$) aryl;

$R_1$, $R_2$, $R_3$, $R_6$, $R_7$, $Y_1$, $Y_2$ and $Y_3$ are each hydrogen; $R_4$ is fluoro, or $OR_{10}$, $R_5$ is $OR_{10}$ or $NR_8R_9$; When $R_5$ is $R_{10}O$, $R_{10}$ is hydrogen or ($C_1$-$C_8$)alkyl; when $R_5$ is $R_8R_9N$, $R_8$ and $R_9$ is selected from hydrogen, ($C_1$-$C_8$) alkyl, ($C_1$-$C_8$) alkoxy, ($C_3$-$C_8$) cycloalkyl, ($C_2$-$C_8$) alkenyl and ($C_2$-$C_8$) alkynyl; wherein said alkyl, alkoxy, alkenyl and alkynyl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, ($C_2$-$C_6$) heterocycloalkyl and ($C_2$-$C_6$) heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, ($C_1$-$C_8$) alkylthio, substituted or unsubstituted amino, hydroxyl, ($C_1$-$C_8$) alkoxyl, carboxyl, amidino and acylamino;

when $N(R_8)(R_9)$ is selected from —$OR_{10}$, —$SR_{10}$, —$N(R_8)$—C(O)$R_{10}$, —$N(R_8)$—C(O)—$OR_{10}$, —$N(R_8)$—C(O)—$NR_8R_{10}$, —$N(R_8)$—C(S)$OR_{10}$, —$N(R_8)$—C(S)—$OR_{10}$, —$N(R_8)$—C(S)—$NR_8R_{10}$; wherein $R_8$ and $R_{10}$ are selected from the group consisting of H, optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

J: X is $N(R_8)$—$SO_2R_{10}$, wherein $R_8$ and $R_{10}$ are each independently selected from the group consisting of hydrogen, ($C_1$-$C_8$) alkyl, ($C_3$-$C_8$) cycloalkyl, ($C_2$-$C_8$) alkenyl and ($C_2$-$C_8$) alkynyl, (C4-C10)aryl; wherein said alkyl, alkenyl, alkynyl and aryl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, and ($C_2$-$C_6$) heterocycloalkyl and ($C_2$-$C_6$) heterocycloaryl groups selected from the group comprising imidizaloly, furyl, tetrahydrofuryl; and if comprising more than two carbon atoms may be branched, cyclic or unbranched or combinations of branched, cyclic and unbranched groups;

R represents, hydrogen, substituted or unsubstituted ($C_1$-$C_6$) alkyl or ($C_1$-$C_6$) alkenyl or ($C_6$-$C_{10}$) aryl;

$R_1$, $R_2$, $R_3$, $R_6$, $R_7$, $Y_1$, $Y_2$ and $Y_3$ are each hydrogen; $R_4$ is fluoro, or $OR_{10}$, $R_5$ is $OR_{10}$ or $NR_8R_9$; When $R_5$ is $R_{10}O$, $R_{10}$ is hydrogen or ($C_1$-$C_8$)alkyl; when $R_5$ is $R_8R_9N$, $R_8$ and R9 is selected from hydrogen, ($C_1$-$C_8$) alkyl, ($C_1$-$C_8$) alkoxy, ($C_3$-$C_8$) cycloalkyl, ($C_2$-$C_8$) alkenyl and ($C_2$-$C_8$) alkynyl; wherein said alkyl, alkoxy, alkenyl and alkynyl are optionally substituted wherein said substituents are selected from the group consisting of halo, cyano, mercapto, ($C_1$-$C_8$) alkylthio, optionally substituted amino, hydroxyl, ($C_1$-$C_8$) alkoxyl, carboxyl, amidino, acylamino, ($C_2$-$C_6$) heterocycloalkyl and ($C_2$-$C_6$) heterocycloaryl and if comprising more than two carbon atoms may be branched, cyclic, unbranched, or combinations of branched, cyclic and unbranched groups;

when $R_5$ is $R_8R_9N$, $R_8$ and $R_9$, together with the nitrogen to which they are attached, form a heterocyclic residue selected from the group consisting of optionally substituted aziridinyl, azetidinyl and pyrrolidinyl wherein said substituents are selected from the group consisting of halo, cyano, mercapto, ($C_1$-$C_8$) alkylthio, substituted or unsubstituted amino, hydroxyl, ($C_1$-$C_8$) alkoxyl, carboxyl, amidino and acylamino;

when $N(R_8)(R_9)$ is selected from —$OR_{10}$, —$SR_{10}$, —$N(R_8)$—$C(O)R_{10}$, —$N(R_8)$—$C(O)$—$OR_{10}$, —$N(R_8)$—$C(O)$—$NR_8R_{10}$, —$N(R_8)$—$C(S)OR_{10}$, —$N(R_8)$—$C(S)$—$OR_{10}$, —$N(R_8)$—$C(S)$—$NR_8R_{10}$; wherein $R_8$ and $R_{10}$ are selected from the group consisting of H, optionally substituted ($C_1$-$C_{20}$) alkyl, optionally substituted ($C_1$-$C_{20}$) heteroalkyl, optionally substituted ($C_2$-$C_{20}$) alkenyl, optionally substituted ($C_2$-$C_{20}$) heteroalkenyl, optionally substituted ($C_2$-$C_{20}$) alkenyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring.

More preferred compounds of the invention are selected from the group consisting of compounds of the formula I, wherein X is selected from the group consisting of —$N(R_8)(R_9)$, —$N(R_8)$—$C(O)R_{10}$, —$N(R_8)$—$C(O)$—$OR_{10}$, —$N(R_8)$—$C(O)$—$NR_8R_{10}$, —$N(R_8)$—$SO2R_{10}$; wherein, $R_8$ and $R_9$ are independently selected from the group consisting of H, optionally substituted ($C_1$-C10) alkyl, optionally substituted aryl, optionally substituted heteroaryl; $R_{10}$ is selected from the group consisting of hydrogen, an optionally substituted ($C_1$-$C_{10}$) alkyl, optionally substituted ($C_4$-$C_{10}$) aryl, optionally substituted ($C_3$-$C_{10}$) heteroaryl; R is selected from the group consisting of an optionally substituted or unsubstituted ($C_1$-$C_6$) alkyl, ($C_4$—C19) aryl, or $COR_8$.

$R_1$ and $R_2$ are each a hydrogen or $R_1$ and $R_2$ together form a single bond;

$R_3$, $R_4$, $Y_1$, $Y_2$, $Y_3$ are independently selected from the group consisting H, halo, —OH; $R_5$ is selected from the group consisting of an optionally substituted ($C_1$-$C1_0$) alkyl, optionally substituted ($C_1$-$C_{10}$) heteroalkyl, optionally substituted ($C_2$-$C_{10}$) alkenyl, optionally substituted ($C_2$-$C_{10}$) heteroalkenyl, optionally substituted ($C_2$-$C_{10}$) alkynyl, optionally substituted ($C_6$-$C_{10}$) aryl, optionally substituted ($C_3$-$C_{10}$) heteroaryl, optionally substituted ($C_7$-$C_{10}$) arylalkyl, optionally substituted ($C_4$-$C_{10}$) heteroarylalkyl, optionally substituted (C3-$C_{10}$) cycloalkyl, optionally substituted ($C_2$-$C_{10}$) cycloheteroalkyl, $N(R_8)(R_9)$; —$OR_{10}$, —$SR_{10}$, —$N(R_8)$—$C(O)R_{10}$, —$N(R_8)$—$C(O)$—$OR_{10}$, —$N(R_8)$—$C(O)$—$NR_8R_{10}$, —$N(R_8)$—$C(S)OR_{10}$, —$N(R_8)$—$C(S)$—$OR_{10}$, and —$N(R_8)$—$C(S)$—$NR_8R_{10}$.

R6 is selected from the group consisting of, hydrogen, hallo, an optionally substituted or unsubstituted ($C_1$-$C_{10}$) alkyl, ($C_1$-$C_{10}$) alkenyl, ($C_6$-$C_{10}$) aryl.

R7 is selected from the group consisted of hydrogen, an optionally substituted ($C_1$-$C_{10}$) alkyl, optionally substituted ($C_5$-$C_{10}$) aryl and optionally substituted ($C_1$-$C_{10}$) acyl.

Formula (I) or pharmacologically acceptable salts thereof may exist in the form of addition products with water or various solvents, and these addition products are also included in the present invention. Examples of formula (J) are shown in Table 1.

TABLE 1

Specific examples of formula (I)

| Compound | $X_1$ | $X_2$ | R |
|---|---|---|---|
| 1 | benzaldehyde | H | H |
| 2 | undecanal | H | H |
| 3 | 4-nitrobenzaldehyde | H | H |
| 4 | 2-(trifluoromethyl)benzaldehyde | H | H |
| 5 | 4-methoxybenzaldehyde | H | H |

TABLE 1-continued

Specific examples of formula (I)

| Compound | X₁ | X₂ | R |
|---|---|---|---|
| 6 | 4-biphenylcarbonyl (C(=O)-C₆H₄-C₆H₅) | H | H |
| 7 | 4-cyanobenzoyl | H | H |
| 8 | 4-fluorobenzoyl | H | H |
| 9 | 3,4-dichlorobenzoyl | H | H |
| 10 | 2-furoyl | H | H |
| 11 | isonicotinoyl (4-pyridylcarbonyl) | H | H |
| 12 | acryloyl (CH₂=CH-C(=O)-) | H | H |
| 13 | COCH₃ | H | H |
| 14 | COCH=CH₂ | H | H |
| 15 | phenyl carbonate (C(=O)-O-C₆H₅) | H | H |
| 16 | COOCH₃ | H | H |
| 17 | COOCH=CH₂ | H | H |
| 18 | COOCH₂CH₃ | H | H |
| 19 | COOCH₂CH₂F | H | H |
| 20 | COO(CH₂)₃CH₃ | H | H |
| 21 | COOCH₂CH₂OCH₃ | H | H |
| 22 | COOCH₂C(CH₃)₃ | H | H |
| 23 | COOCH₂(CH₂)₄CH₃ | H | H |
| 24 | COOCH₂(CH₂)₁₀CH₃ | H | H |
| 25 | benzyl carbonate (C(=O)-O-CH₂-C₆H₅) | H | H |
| 26 | 4-fluorophenyl carbonate | H | H |
| 27 | 4-methoxyphenyl carbonate | H | H |
| 28 | 4-(trifluoromethyl)phenylsulfonyl | H | H |
| 29 | methanesulfonyl | H | H |
| 30 | ethanesulfonyl | H | H |

TABLE 1-continued

Specific examples of formula (I)

| Compound | X₁ | X₂ | R |
|---|---|---|---|
| 31 | cyclopropyl-SO₂- | H | H |
| 32 | n-propyl-SO₂- | H | H |
| 33 | phenyl-SO₂- | H | H |
| 34 | CF₃CH₂-SO₂- | H | H |
| 35 | benzyl-SO₂- | H | H |
| 36 | 4-methylphenyl-SO₂- | H | H |
| 37 | 4-fluorophenyl-SO₂- | H | H |
| 38 | 4-methoxyphenyl-SO₂- | H | H |
| 39 | 2,6-difluorophenyl-SO₂- | H | H |
| 40 | 3,4-difluorophenyl-SO₂- | H | H |
| 41 | n-heptyl-SO₂- | H | H |
| 42 | 4-isopropylphenyl-SO₂- | H | H |
| 43 | naphthalen-2-yl-SO₂- | H | H |
| 44 | 3-chloro-4-fluorophenyl-SO₂- | H | H |
| 45 | 4-acetamidophenyl-SO₂- | H | H |

TABLE 1-continued

Specific examples of formula (I)

| Compound | X₁ | X₂ | R |
|---|---|---|---|
| 46 | 3,4-dimethoxyphenylsulfonyl (SO₂-C₆H₃(OCH₃)₂) | H | H |
| 47 | biphenyl-4-ylsulfonyl | H | H |
| 48 | CHO-NH-C₆H₅ (formanilide) | H | H |
| 49 | CONHCH=CH₂ | H | H |
| 50 | CONHCH₂CH₃ | H | H |
| 51 | CONHCH₂CH=CH₂ | H | H |
| 52 | CONHCH₂CH₂CH₃ | H | H |
| 53 | CONHC(CH₃)₃ | H | H |
| 54 | CONHCOOCH₃ | H | H |
| 55 | CONHCH₂(CH₂)₄CH₃ | H | H |
| 56 | CHO-NH-cyclopentyl | H | H |
| 57 | CHO-NH-(furan-2-yl) | H | H |
| 58 | CHO-NH-cyclohexyl | H | H |
| 59 | CHO-NH-CH₂-C₆H₅ | H | H |
| 60 | CHO-NH-C₆H₄-4-F | H | H |
| 61 | CHO-NH-C₆H₃-2,6-(CH₃)₂ | H | H |
| 62 | CHO-NH-C₆H₄-4-OCH₃ | H | H |
| 63 | CHO-NH-C₆H₄-4-N(CH₃)₂ | H | H |
| 64 | CH₃ | H | H |
| 65 | CH₂CH₃ | H | H |
| 66 | CH₂CH=CH₂ | H | H |
| 67 | (CH₂)₅CH₃ | H | H |
| 68 | (CH₂)₁₁CH₃ | H | H |
| 69 | CHO-C₆H₃-3,4-Cl₂ | H | CH₃ |
| 70 | COCH₃ | H | CH₃ |
| 71 | COCH₂(CH₂)₄CH₃ | H | CH₃ |
| 72 | COCH₂CH₂F | H | CH₃ |
| 73 | CHO-(CH₂)₁₀CH₃ (dodecanoyl) | H | CH₃ |

TABLE 1-continued

Specific examples of formula (I)

[Macrocyclic structure with substituents X₁, X₂, and R as shown at top of both columns]

| Compound | X₁ | X₂ | R |
|---|---|---|---|
| 74 | 4-nitrobenzoyl (C(=O)-C₆H₄-NO₂) | H | CH₃ |
| 75 | 2-(trifluoromethyl)benzoyl | H | CH₃ |
| 76 | 4-methoxybenzoyl | H | CH₃ |
| 77 | 4-biphenylcarbonyl | H | CH₃ |
| 78 | 4-cyanobenzoyl | H | CH₃ |
| 79 | 4-fluorobenzoyl | H | CH₃ |
| 80 | 2-furoyl | H | CH₃ |
| 81 | isonicotinoyl (pyridine-4-carbonyl) | H | CH₃ |
| 82 | acryloyl (CH=CH₂-C(=O)) | H | CH₃ |
| 83 | COCH₃ | H | CH₃ |
| 84 | COCH=CH₂ | H | CH₃ |
| 85 | phenoxycarbonyl (COO-C₆H₅) | H | CH₃ |
| 86 | COOCH₃ | H | CH₃ |
| 87 | COOCH=CH₂ | H | CH₃ |
| 88 | COOCH₂CH₃ | H | CH₃ |
| 89 | COOCH₂CH₂F | H | CH₃ |
| 90 | COO(CH₂)₃CH₃ | H | CH₃ |
| 91 | COOCH₂CH₂OCH₃ | H | CH₃ |
| 92 | COOCH₂C(CH₃)₃ | H | CH₃ |
| 93 | COOCH₂(CH₂)₄CH₃ | H | CH₃ |
| 94 | benzyloxycarbonyl (COO-CH₂-C₆H₅) | H | CH₃ |
| 95 | (4-fluorophenoxy)carbonyl | H | CH₃ |

TABLE 1-continued

Specific examples of formula (I)

| Compound | X₁ | X₂ | R |
|---|---|---|---|
| 96 | 4-methoxyphenyl formate (O-C(=O)-O-C₆H₄-OCH₃) | H | CH₃ |
| 97 | 4-(trifluoromethyl)phenylsulfonyl | H | CH₃ |
| 98 | methylsulfonyl | H | CH₃ |
| 99 | ethylsulfonyl | H | CH₃ |
| 100 | cyclopropylsulfonyl | H | CH₃ |
| 101 | butylsulfonyl | H | CH₃ |
| 102 | phenylsulfonyl | H | CH₃ |
| 103 | 2,2,2-trifluoroethylsulfonyl | H | CH₃ |
| 104 | benzylsulfonyl | H | CH₃ |
| 105 | 4-methylphenylsulfonyl | H | CH₃ |
| 106 | 4-fluorophenylsulfonyl | H | CH₃ |
| 107 | 4-methoxyphenylsulfonyl | H | CH₃ |
| 108 | 2,6-difluorophenylsulfonyl | H | CH₃ |
| 109 | 3,4-difluorophenylsulfonyl | H | CH₃ |
| 110 | octylsulfonyl | H | CH₃ |
| 111 | 4-isopropylphenylsulfonyl | H | CH₃ |

TABLE 1-continued

Specific examples of formula (I)

[Structure: macrocyclic compound with X₁X₂N- substituent, OMe, OR, OH, MeO, OCONH₂ groups]

| Compound | X₁ | X₂ | R |
|---|---|---|---|
| 112 | 2-naphthylsulfonyl (SO₂-2-naphthyl) | H | CH₃ |
| 113 | 3-chloro-4-fluorophenylsulfonyl | H | CH₃ |
| 114 | 4-(acetylamino)phenylsulfonyl | H | CH₃ |
| 115 | 3,4-dimethoxyphenylsulfonyl | H | CH₃ |
| 116 | 4-biphenylsulfonyl | H | CH₃ |
| 117 | CHO-NH-phenyl (phenylaminocarbonyl-formyl) | H | CH₃ |
| 118 | CONHCH=CH₂ | H | CH₃ |
| 119 | CONHCH₂CH₃ | H | CH₃ |
| 120 | CONHCH₂CH=CH₂ | H | CH₃ |
| 121 | CONHCH₂CH₂CH₃ | H | CH₃ |
| 122 | CONHC(CH₃)₃ | H | CH₃ |
| 123 | CONHCOOCH₃ | H | CH₃ |
| 124 | CONHCH₂(CH₂)₄CH₃ | H | CH₃ |
| 125 | cyclopentyl-NH-CHO | H | CH₃ |

TABLE 1-continued

Specific examples of formula (I)

[Structure: macrocyclic compound with X₁X₂N- substituent, OMe, OR, OH, MeO, OCONH₂ groups]

| Compound | X₁ | X₂ | R |
|---|---|---|---|
| 126 | 2-furyl-NH-CHO | H | CH₃ |
| 127 | cyclohexyl-NH-CHO | H | CH₃ |
| 128 | benzyl-NH-CHO | H | CH₃ |
| 129 | 4-fluorophenyl-NH-CHO | H | CH₃ |
| 130 | 2,6-dimethylphenyl-NH-CHO | H | CH₃ |
| 131 | 4-methoxyphenyl-NH-CHO | H | CH₃ |
| 132 | 4-(dimethylamino)phenyl-NH-CHO | H | CH₃ |
| 133 | CH₃ | H | CH₃ |
| 134 | CH₂CH₃ | H | CH₃ |
| 135 | CH₂CH=CH₂ | H | CH₃ |
| 136 | (CH₂)₅CH₃ | H | CH₃ |
| 137 | (CH₂)₁₁CH₃ | H | CH₃ |
| 138 | CH₃ | H | CH₃ |
| 139 | CH₂CH₃ | H | CH₃ |

TABLE 1-continued

Specific examples of formula (I)

[Structure of formula I showing a macrocyclic ansamycin with substituents $X_1$, $X_2$ on N, OR, MeO, OH, OCONH$_2$ groups]

| Compound | $X_1$ | $X_2$ | R |
|---|---|---|---|
| 140 | (CH$_2$)$_5$CH$_3$ | H | CH$_3$ |
| 141 | (CH$_2$)$_{11}$CH$_3$ | H | CH$_3$ |

The pharmacologically acceptable salts of formula (I) include acid addition salts, metal salts, ammonium salts, organic amine addition salts, amino acid addition salts, and the like. Examples of the acid addition salts include inorganic acid salts (for example, hydrochloride, hydrobromide, sulfate, phosphate, and the like), and organic acid salts (for example, formate, acetate, oxalate, benzoate, methanesulfonate, p-toluenesulfonate, maleate, fumarate, tartrate, citrate, succinate, lactate, and the like). Examples of the metal salts include alkali metal salts (for example, lithium salt, sodium salt, potassium salt, and the like), alkaline earth metal salts (for example, magnesium salt, calcium salt, and the like), aluminum salts, zinc salts, and the like. Examples of the ammonium salts include salts with ammonium, tetramethylammonium, and the like. Examples of the organic amine addition salts include addition salts with morpholine, piperidine, and the like. Examples of the amino acid addition salts include addition salts with glycine, phenylalanine, aspartic acid, glutamic acid, lysine, and the like.

In another embodiment, a method of preparing the inventive compounds is provided. The compounds of the present invention are generally prepared using geldanamycin as a starting material. Compound (I) may contain various stereoisomers, geometric isomers, tautomeric isomers, and the like. All of possible isomers and their mixtures are included in the present invention, and the mixing ratio is not particularly limited.

The synthetic method of formula (I) mainly comprises 18-substituted amide geldanamycin production and their 21-methoxyl derivatives (Step 2), 18-substituted sulfoamido formation and their 21-methoxyl derivatives (Step 2), 18-substituted carbamate formation and their 21-methoxyl derivatives (Step 2), 18-substituted carbamide formation and their 21-methoxyl derivatives (step 3), 18-substituted amino production and their 21-methoxyl derivatives (Step 4).

The general procedure for preparation of 18-amino-21-hydroxyl geldanamycin intermediate C is showed in Step 1. For example, Formula B can be prepared by oxime formation from Compound A and the following formula H$_2$N—O—R$_{3a}$ (II) (where R$_{3a}$ is a group in which COR$_{10}$ wherein R$_{10}$ has the same meaning as described above) or an acid addition salt thereof. And then reduction of benzoquinone imine moiety of ansamycin derivative B to form intermediate C.

Examples of suitable reaction solvents for oxime formation reaction include, but are not limited to, pyridine, chloroform, dichloromethane, ethyl acetate, ether, tetrahydrofuran (THF), dimethylformamide (DMF), acetonitrile, and the like, which may be used either alone or as a mixture thereof. A preferred solvent is pyridine. Examples of suitable acids include hydrochloric acid, acetic acid, trifluoroacetic acid, sulfuric acid, p-toluenesulfonic acid, camphorsulfonic acid, and the like. The acids are preferably used in an amount of 0.1 to 10 equivalents based on compound A. When an acid addition salt of formula (II) is used, the reaction can be carried out in the presence of a base, for example, an amine (e.g., pyridine, triethylamine, diisopropylethylamine, N,N-dimethylaniline, N,N-diethylaniline, or the like), an alkali metal, carbonate, or bicarbonate (e.g., sodium carbonate, potassium carbonate, or the like), in an amount of 1 equivalent or more based on the acid addition salt of formula (II). In a preferred embodiment, pyridine is used as both the amine and the solvent. The reaction is carried out at a temperature of −20 to 100° C., preferably 20 to 80° C., and the reaction completes after 1 to 80 hours.

A variety of method and reaction condition can be used to reduce the benzoquinone imine portion of the ansamycin. Sodium hydrosulfite may be used as the reducing agent. Other reducing agents that can be used include, but are not limited to, zinc dust with acetic anhydride or acetic acid, ascorbic acid and electrochemical reductions.

Reduction of benzoquinone moiety of the ansamycin derivatives B may be accomplished using sodium hydrosulfite in a biphasic reaction mixture. Typically, the ansamycin derivative B is dissolved in an organic solvent, such as ethyl acetate. Other solvents that can be used include, but are not limited to, dichloromethane, chloroform, dichloroethane, chlorobenzene, THF, MeTHF, diethyl ether, diglyme, 1,2-dimethoxyethane, MTBE, THP, dioxane, 2-ethoxybutane, methyl butyl ether, methyl acetate, 2-butanone, water and mixture thereof. Two or more equivalents of sodium hydrosulfite are then added as a solution in water (5-30% (m/v), preferably 110% (m/v), to the reaction vessel at room temperature. Aqueous solutions of sodium hydrosulfite are unstable and therefore need to be freshly prepared just prior to use. Vigorous mixing of the biphasic mixture ensures reasonable reaction rates.

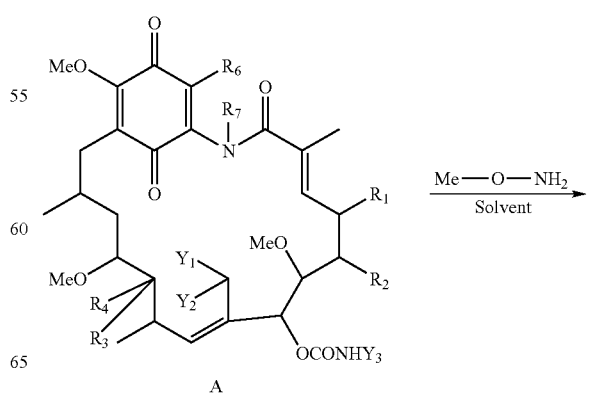

A

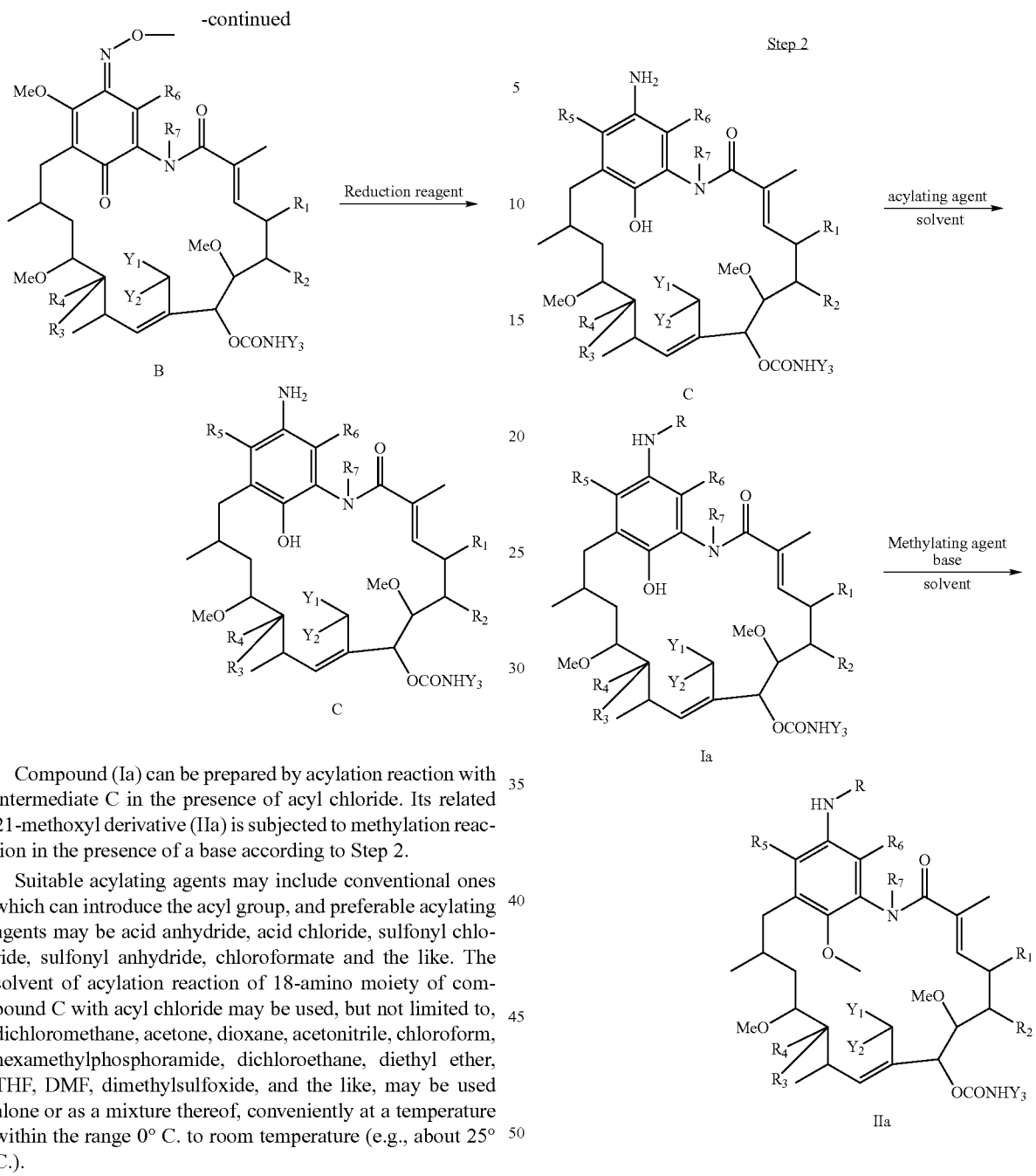

Compound (Ia) can be prepared by acylation reaction with intermediate C in the presence of acyl chloride. Its related 21-methoxyl derivative (IIa) is subjected to methylation reaction in the presence of a base according to Step 2.

Suitable acylating agents may include conventional ones which can introduce the acyl group, and preferable acylating agents may be acid anhydride, acid chloride, sulfonyl chloride, sulfonyl anhydride, chloroformate and the like. The solvent of acylation reaction of 18-amino moiety of compound C with acyl chloride may be used, but not limited to, dichloromethane, acetone, dioxane, acetonitrile, chloroform, hexamethylphosphoramide, dichloroethane, diethyl ether, THF, DMF, dimethylsulfoxide, and the like, may be used alone or as a mixture thereof, conveniently at a temperature within the range 0° C. to room temperature (e.g., about 25° C.).

The methylation reagent for 21-hydroxyl moiety of the Compound 1a may be used methiodide, but not limited to, methyl sulfate, azimethane, dimethyl sulfate and, TMSCHN$_2$, methyl p-toluenesulfonate.

The methylation is preferably effected in the presence of a suitable acid scavenger, for example, inorganic bases such as sodium or potassium hydride, sodium, lithium or potassium carbonate, sodium or potassium hydroxide, organic bases such as triethylamine, diisopropylethylamine, tetraethylammonium fluoride or pyridine. The reaction is conveniently effected in a solvent such as DMF, THF, acetonitrile, diethyl ether, dioxane, dichloromethane or chloroform at a temperature between ambient and the reflux temperature of the solvent.

As illustrated in Step 3, Formula (Ib) can be prepared by the condensation reaction with substituted isocyanate in the suitable solvent. The further methylation reaction is subjected to get compound (IIb) with the same reaction condition as Step 2.

The solvents of condensation reaction of 18-amino moiety of compound C with isocynate may be used, but not limited to, dichloromethane, acetone, dioxane, acetonitrile, chloroform, hexamethylphosphoramide, dichloroethane, diethyl ether, THF, DMF, dimethylsulfoxide, and the like, may be used alone or as a mixture thereof, conveniently at a temperature within the range 0° C. to room temperature (e.g., about 25° C.).

Step 3

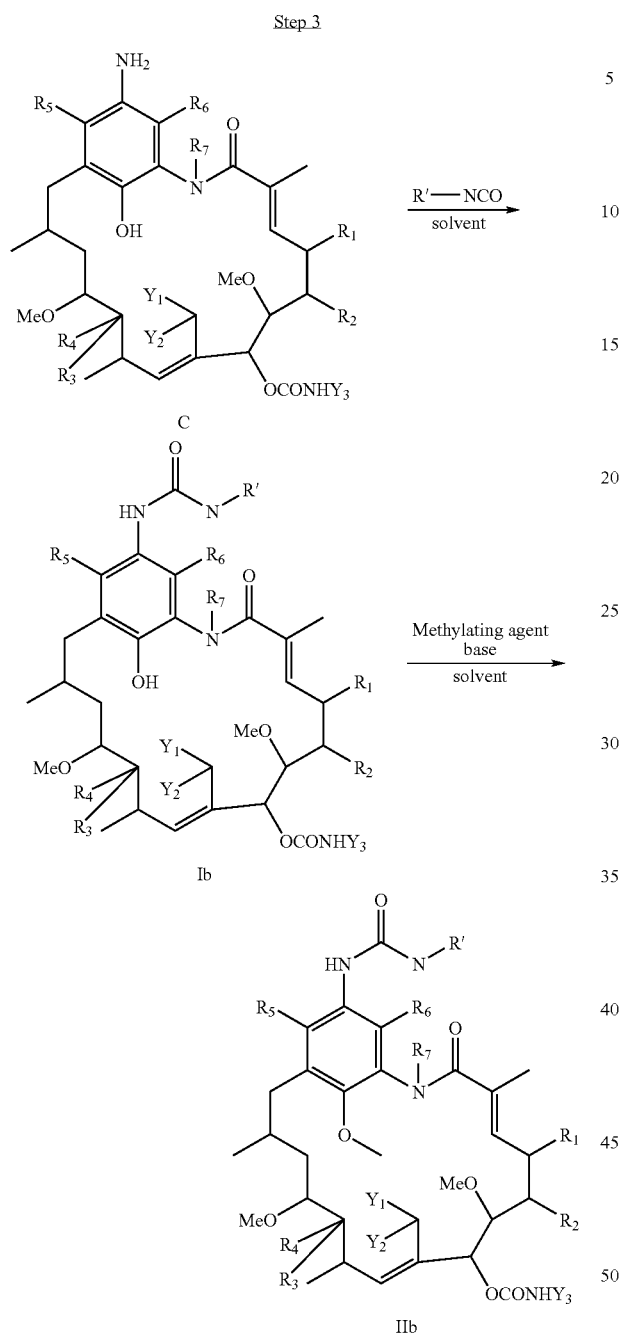

As illustrated in Step 4, Formula (Ic) can be prepared by condensation reaction with substituted aldehyde or ketone (Where R'COR"; wherein R' or R" independently or together represents hydrogen, the substituted or unsubstituted ($C_1$-$C_{10}$) allyl or alkenyl), and then the further reduction reaction. The further methylation reaction is subjected to get compound (IIc) with the same reaction condition as Step 2.

The solvent of condensation reaction may be used, but not limited to, dichloromethane, acetone, dioxane, acetonitrile, chloroform, dichloroethane, diethyl ether, THF, DMF, and the like, may be used alone or as a mixture thereof, conveniently at a temperature within the range −60° C. to room temperature (e.g., about 25° C.).

A variety of reducing agent and reaction condition can be used to reduce imine. Sodium cyanoborohydride may be used as the reducing agent, other reducing agents that can be used include, but are not limited to, sodium borohydride, sodium dithionite, lithium aluminum hydride, Red-Al, and the like. The solvent maybe used, but not limited to, alcoholic solvents such as methanol and ethanol under neutral conditions at temperatures range from 0° C. to that of the refluxing solvent, DMF, acetonitrile, benzene, toluene, and the like.

Step 4

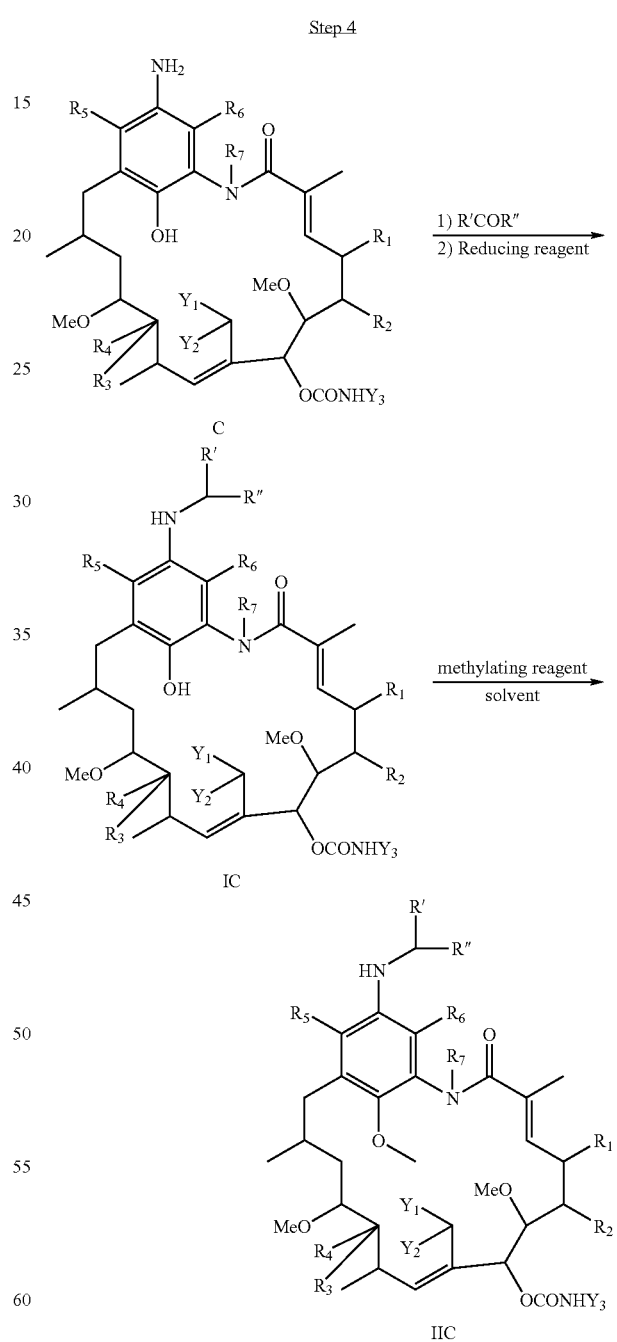

The lipophilic compounds of this invention will more easily pass through the cell membranes and distribute across tissues and the blood brain barrier. Such tissue includes the blood and blood forming system including platelets, blood vessel wall, and bone marrow; the cardiovascular system including heart and vascular system; digestive and excretory system including alimentary tract, biliary tract, kidney, liver, pancreas and urinary tract; the endocrine system including adrenal gland, kidney, ovary, pituitary gland, renal gland, salivary gland, sebaceous gland, testis, thymus gland and thyroid gland; the muscular system; reproductive system, including breast, ovary, penis and uterus; the respiratory system including bronchus, lung and trachea; skeletal system including bones and joints; tissue, fiber, and integumentary system including adipose tissue, cartilage, connective tissue, cuticle, dermis, epidermis, epithelium, fascia, hair follicle, ligament, bone marrow, melanin, melanocyte, mucous membrane, skin, soft tissue, synovial capsule and tendon.

Compounds of the present invention preferably have a strong binding affinity for Hsp90. A preferred method of determining the relative binding affinities is by comparing the concentration of the test compound at which 50% of the target-protein is bound (otherwise known as the $IC_{50}$ concentration level) in a competitive binding assay.

Geldanamycin analogs of Formula (I) in this invention can be used in accordance with the methods of the present invention to alter the function of hormone receptors, making it easier to inhibit the associated signal pathways using low levels of a second drug which targets the proteins involved in those signaling pathways. Such a combination therapy can be useful to reduce non-specific toxicity associated with therapy by reducing the level of the drug required.

The present invention provides compositions of matter that are formulations of one or more active drugs and a pharmaceutically-acceptable carrier. In this regard, the invention provides a composition for administration to a mammalian subject, which may include a plurality of particles of the compound of formula I. In a preferred embodiment, the average size of the particles is no greater than about 500 nm, preferably no greater than 400 nm, more preferably no greater than 200 nm.

The compounds of the present invention may be administered as a pharmaceutical composition containing the compounds and a pharmaceutically-acceptable carrier or diluent. The active materials can also be mixed with other active materials which do not impair the desired action and/or supplement the desired action. The active materials, in accordance with the present invention, may be administered by any acceptable route including, but not limited to, orally, parenterally, intravenously, intradermally, subcutaneously, intramuscularly, by an airborne delivery system, topically, in liquid or solid form.

Oral compositions will generally include an inert diluent or an edible carrier. Such oral compositions may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

In accordance with the invention, there are provided compositions containing geldanamycin derivatives and methods useful for the in vivo delivery of geldanamycin derivatives in the form of nanoparticles, which are suitable for any of the aforesaid routes of administration.

U.S. Pat. Nos. 5,916,596, 6,506,405 and 6,537,579 teach the preparation of nanoparticles from the biocompatible polymers, such as albumin. Thus, in accordance with the present invention, there are provided methods for the formation of nanoparticles of the present invention by a solvent evaporation technique from an oil-in-water emulsion prepared under conditions of high shear forces (e.g., sonication, high pressure homogenization, or the like).

In accordance with the invention, the compounds of the invention may be used to treat diseases associated with cellular proliferation or hyperproliferation, such as cancers which include but are not limited to tumors of the nasal cavity, paranasal sinuses, nasopharynx, oral cavity, oropharynx, larynx, hypopharynx, salivary glands, and paragangliomas. The compounds of the invention may also be used to treat cancers of the liver and biliary tree (particularly hepatocellular carcinoma), intestinal cancers, particularly colorectal cancer, ovarian cancer, small cell and non-small cell lung cancer, breast cancer, sarcomas (including fibrosarcoma, malignant fibrous histiocytoma, embryonal rhabdomysocarcoma, leiomyosarcoma, neuro-fibrosarcoma, osteosarcoma, synovial sarcoma, liposarcoma, and alveolar soft part sarcoma), neoplasms of the central nervous systems (particularly brain cancer), and lymphomas (including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma).

The invention also provides methods of treating a mammal afflicted with the above diseases and conditions. The method includes administering one or more of the inventive compounds to the afflicted mammal. The method may further include the administration of a second active agent, such as a cytotoxic agent, including alkylating agents, tumor necrosis factors, intercalators, microtubulin inhibitors, and topoisomerase inhibitors. The second active agent may be co-administered in the same composition or in a second composition. Examples of suitable second active agents include, but are not limited to, a cytotoxic drug such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride. In accordance with the invention, the compounds and compositions may be used at sub-cytotoxic levels in combination with other agents in order to achieve highly selective activity in the treatment of non-neoplastic disorders, such as heart disease, stroke and neurodegenerative diseases. See Whitesell et al., Curr Cancer Drug Targets. 2003, 3(5), 349-58. In this embodiment, the compounds useful in the methods of the invention are used to reduce the cellular levels of Hsp90 client proteins, which are then effectively inhibited by the second agent. Binding of the client proteins to Hsp90 stabilizes the client proteins and maintains them in a soluble, inactive form ready to respond to activating stimuli. Binding of a geldanamycin derivative to Hsp90 results in targeting the client protein to the proteasome, and subsequent degradation. For systems such as a steroid receptor, however, Hsp90 forms an integral part of the functional receptor complex along with several other proteins such as Hsp70, Hsp40, p23, hip, Hsp56, and immunophilins. Hsp90 appears to regulate the activity of the steroid receptor by maintaining the receptor in a high-affinity hormone-binding conformation.

The following examples further illustrate the invention but, of course, should not be construed as in any way limiting its scope.

Example 1

This example demonstrates the preparation of 18-N-Benzamide-21-hydroxylgeldanamycin (1)

To a solution of geldanamycin (300.0 mg, 0.535 mmol) in pyridine was added o-methylamine hydrochloride (446.7 mg, 5.35 mmol), and the mixture was then stirred at 80° C. for 30 min, and then removed the pyridine completely by vacuum. The residue was purified by column chromatography, eluting with $CH_2Cl_2$/MeOH (98:2) to give 18-methoximino geldanamycin as yellow solid (218.1 mg, 69.1% yield).

A solution of 18-methoximino geldanamycin (105.9 mg, 0.18 mmol) in EtOAc (10 mL) was treated with $Na_2S_2O_4$ (8 mL, 10%) at RT. After 3 h, the aqueous layer was extracted twice with EtOAC and the combined organic layers were dried over $Na_2S_2O_4$, concentrated under reduced pressure to give 18-amino-21-hydroxylgeldanamycin as yellow solid. This latter was dissolved into anhydrous $CH_2Cl_2$ under argon atmosphere and to the resulting solution was added benzoic chloride at 0° C. After 12 h at RT, the reaction mixture was diluted with $CH_2Cl_2$, washed with sat. $NaHCO_3$, and dried over $Na_2SO_4$, after filtration and removed the solvent under reduced pressure, the crude product was purified by flash chromatography to give 1 as pale solid (45.0 mg, yield 37.6%). $^1$H NMR (1, $CDCl_3$, 500 MHz) δ 8.80 (s, 1H), 8.69 (brs, 1H), 8.60 (brs, 1H), 8.24 (s, 1H), 7.86 (d, J=7.5 Hz, 2H), 7.52 (t, J=7.5 Hz, 1H), 7.47 (t, J=7.5 Hz, 2H), 6.94 (d. J=9.5 Hz, 1H), 6.47 (t, J=11.0 Hz, 1H), 5.74-5.72 (m, 2H), 5.41 (brs, 2H), 5.02 (s, 1H), 4.29 (d, J=9.0 Hz, 1H), 3.65-3.56 (m, 4H), 3.43 (d, J=0.5 Hz, 1H), 3.33 (s, 3H), 3.22 (s, 3H), 2.76-2.62 (m, 3H), 1.94 (s, 3H), 1.84-1.81 (m, 2H), 1.74 (s, 3H), 1.69-1.66 (m, 1H), 0.93-0.86 (m, 6H); MS (ESI) Calcd. for ($C_{36}H_{47}N_3O_9$): 665, found 688 (MNa$^+$), 664 (M-H)$^-$.

Example 2

This example demonstrates the preparation of 18-N-Lauramide-21-hydroxylgeldanamycin (2)

Compounds 2 (25.0 mg, 18.7% yield) as pale solid was prepared from 18-methoximino geldanamycin (0.180 mmol) and lauroyl chloride (19.6 mg, 0.09 mmol) in the same manner as described for 1.

$^1$H NMR (2, $CDCl_3$, 500 MHz) δ 8.68 (brs, 1H), 8.44 (s, 1H), 8.24 (brs, 1H), 7.49 (s, 1H), 6.95 (d, J=11.0 Hz, 1H), 6.46 (t, J=1.5 Hz, 1H), 5.76 (t, J=9.5 Hz, 1H), 5.70 (d, J=8.0 Hz, 1H), 5.18 (s, 1H), 5.06 (s, 2H), 4.29 (d, J=8.5 Hz, 1H), 3.50-3.49 (m, 1H), 3.34 (m, 4H), 3.26 (s, 3H), 2.76-2.72 (m, 1H), 2.68-2.63 (m, 1H), 2.48-2.46 (m, 1H), 2.33 (t, J=6.5 Hz, 2H), 1.95 (s, 3H), 1.74 (s, 3H), 1.69-1.66 (m, 1H), 1.21-1.45 (m, 20H), 0.96-0.95 (m, 3H), 0.87-0.82 (m, 6H); MS (ESI) Calcd. for ($C_{41}H_{65}N_3O_9$): 743, found 766 (MNa$^+$), 744 (M-H)$^-$.

Example 3

This example demonstrates the preparation of 18-N-(4-Nitro)benzamide-21-hydroxylgeldanamycin (3)

Compounds 3 (81.8 mg, 52.9% yield) as pale solid was prepared from 18-methoximino geldanamycin (0.218 mmol) and 4-nitrobenzoyl chloride (28.3 mg, 0.1525 mmol) in the same manner as described for 1.

$^1$H NMR (3, MeOD, 500 MHz) δ 8.44 (d, J=8.5 Hz, 2H), 8.11 (d, J=8.5 Hz, 2H), 7.95 (s, 1H), 6.43 (t, J=11.5 Hz, 1H), 6.18 (d, J=11.5 Hz, 1H), 5.12-5.05 (m, 2H), 4.83 (d, J=9.5 Hz, 1H), 3.96 (t, J=10.0 Hz, 1H), 3.71 (s, 3H), 3.62 (d, J=10.0 Hz, 1H), 3.32-3.28 (m, 1H), 3.30 (s, 3H), 3.10 (s, 3H), 2.92 (d, J=10.0 Hz, 1H), 2.84 (d, J=11.0 Hz, 1H), 2.74-2.71 (m, 1H), 2.39-2.34 (m, 1H), 2.20-2.10 (m, 1H), 2.05 (s, 3H), 1.79-1.71 (m, 1H), 1.16 (s, 3H), 0.96 (d, J=6.5 Hz, 3H), 0.68 (d, J=6.5 Hz, 3H); MS (ESI) Calcd. for ($C_{36}H_{46}N_4O_{11}$): 710, found 733 (MNa$^+$), 709 (M-H)$^-$.

Example 4

This example demonstrates the preparation of 18-N-(2-Trifluoro)benzamide-21-hydroxylgeldanamycin (4)

Compounds 4 (106.5 mg, 62.3% yield) as pale solid was prepared from 18-methoximino geldanamycin (0.233 mmol) and 2-trifluorobenzoyl chloride (34.0 mg, 0.1631 mmol) in the same manner as described for 1.

$^1$H NMR (4, MeOD, 500 MHz) δ 7.89 (d, J=8.0 Hz, 1H), 7.81 (s, 1H), 7.84-7.81 (m, 1H), 7.74 (t, J=7.5 Hz, 1H), 7.69 (d, J=8.0 Hz, 1H), 6.44 (t, J=11.5 Hz, 1H), 6.18 (d, J=11.5 Hz, 1H), 5.15-5.08 (m, 2H), 4.86 (d, J=9.5 Hz, 1H), 4.00 (t, J=10 Hz, 1H), 3.65 (s, 3H), 3.62 (d, J=10 Hz, 1H), 3.34 (brs, 1H), 3.31 (s, 3H), 3.13 (s, 3H), 2.91 (dd, J=13.0 and 3.0 Hz, 1H), 2.84 (d, J=11.5 Hz, 1H), 2.73-2.71 (m, 1H), 2.35-2.29 (m, 1H), 2.20 (brs, 1H), 2.07 (s, 3H), 1.76-1.71 (m, 1H), 1.20 (s, 3H), 0.94 (d, J=6.5 Hz, 3H), 0.68 (d, J=6.5 Hz, 3H); MS (ESI) Calcd. for ($C_{37}H_{46}F_3N_3O_9$): 733, found 733 (MNa$^+$), 732 (M-H)$^-$.

Example 5

This example demonstrates the preparation of 18-N-(4-Methoxy)benzamide-21-hydroxylgeldanamycin (5)

Compounds 5 (68.1 mg, 42.0% yield) as pale solid was prepared from 18-methoximino geldanamycin (0.233 mmol) and 4-methoxylbenzoyl chloride (27.8 mg, 0.1631 mmol) in the same manner as described for 1.

$^1$H NMR (5, MeOD, 500 MHz) δ 7.92 (d, J=9.0 Hz, 2H), 7.88 (s, 1H), 7.11 (d, J=8.5 Hz, 2H), 6.43 (t, J=11.0 Hz, 1H), 6.18 (d, J=11.0 Hz, 1H), 5.14-5.06 (m, 2H), 4.84 (d, J=9.5 Hz, 1H), 3.96 (t, J=10.0 Hz, 1H), 3.90 (s, 3H), 3.69 (s, 3H), 3.63 (d, J=10.0 Hz, 1H), 3.33-3.28 (m, 1H), 3.31 (s, 3H), 3.09 (s, 3H), 2.91 (d, J=10.5 Hz, 1H), 2.85 (d, J=10.5 Hz, 1H), 2.72 (d, J=11.5 Hz, 1H), 2.40-2.39 (m, 1H), 2.19 (brs, 1H), 2.05 (s, 3H), 1.79-1.72 (m, 1H), 1.17 (s, 3H), 0.99 (d, J=6.0 Hz, 3H), 0.69 (d, J=5.0 Hz, 3H); MS (ESI) Calcd. for ($C_{37}H_{49}N_3O_{10}$): 695, found 718 (MNa$^+$), 694 (M-H)$^-$.

Example 6

This example demonstrates the preparation of 18-N-(4-Phenyl)benzamide-21-hydroxylgeldanamycin (6)

Compounds 6 (83.8 mg, 58.7% yield) as pale solid was prepared from 18-methoximino geldanamycin (0.192 mmol) and 4-phenylbenzyl chloride (33.3 mg, 0.154 mmol) in the same manner as described for 1.

$^1$H NMR (6, $CDCl_3$+MeOD, 500 MHz) δ 8.51 (s, 1H), 7.88 (d, J=8.5 Hz, 2H), 7.62 (d, J=8.0 Hz, 2H), 7.54 (d, J=7.5 Hz, 2H), 7.39 (t, J=7.5 Hz, 2H), 7.31 (t, J=7.5 Hz, 1H), 6.88 (d, J=12.0 Hz, 1H), 6.46 (t, J=11.0 Hz, 1H), 5.66-5.62 (m, 2H), 4.92 (s, 1H), 4.24 (d, J=9.5 Hz, 1H), 3.62 (s, 3H), 3.46 (d, J=9.0 Hz, 1H), 3.30 (d, J=9.0 Hz, 1H), 3.27 (s, 3H), 3.19 (s, 3H), 2.67-2.63 (m, 2H), 2.53 (d, J=12.5 Hz, 1H), 1.92 (s, 3H), 1.77-1.75 (m, 2H), 1.64 (s, 3H), 1.57-1.55 (m, 1H), 0.88 (d, J=5.0 Hz, 3H), 0.78 (d, J=7.0 Hz, 3H); MS (ESI) Calcd. for ($C_{42}H_{51}N_3O_9$): 741, found 764 (MNa$^+$), 740 (M-H)$^-$.

Example 7

This example demonstrates the preparation of 18-N-(4-Cyano)benzamide-21-hydroxylgeldanamycin (7)

Compounds 7 (45.4 mg, 34.2% yield) as pale solid was prepared from 18-methoximino geldanamycin (0.192 mmol) and 4-cyanobenzoyl chloride (31.8 mg, 0.154 mmol) in the same manner as described for 1.

$^1$H NMR (7, MeOD, 500 MHz) δ 8.05 (d, J=8.5 Hz, 2H), 7.96 (d, J=8.0 Hz, 2H), 7.93 (s, 1H), 6.43 (t, J=11.5 Hz, 1H), 6.17 (d, J=111.5 Hz, 1H), 5.13-5.06 (m, 2H), 4.83 (d, J=9.5 Hz, 1H), 3.96 (t, J=10.0 Hz, 1H), 3.69 (s, 3H), 3.62 (d, J=10.0 Hz, 1H), 3.33-3.27 (m, 1H), 3.30 (s, 3H), 3.09 (s, 3H), 2.91 (d, J=110.0 Hz, 1H), 2.84 (d, J=11.0 Hz, 1H), 2.71 (d, J=11.5 Hz, 1H), 2.39-2.36 (m, 1H), 2.18 (brs, 1H), 2.05 (s, 3H), 1.79-1.71 (m, 1H), 1.15 (s, 3H), 0.96 (d, J=6.0 Hz, 3H), 0.69 (d, J=6.0 Hz, 3H); MS (ESI) Calcd. for ($C_{37}H_{46}N_4O_9$): 690, found 713 (MNa$^+$), 689 (M-H)$^-$.

Example 8

This example demonstrates the preparation of 18-N-(4-Fluoro)benzamide-21-hydroxylgeldanamycin (8)

Compounds 8 (62.2 mg, 40.9% yield) as pale solid was prepared from 18-methoximino geldanamycin (0.222 mmol) and 4-fluorobenzoyl chloride (28.2 mg, 0.178 mmol) in the same manner as described for 1.

$^1$H NMR (8, MeOD, 500 MHz) δ 7.98 (dd, J=5.5 and 8.5 Hz, 2H), 7.89 (s, 1H), 7.33 (t, J=8.5 Hz, 2H), 6.43 (t, J=11.5 Hz, 1H), 6.17 (d, J=11.5 Hz, 1H), 5.13-5.02 (m, 2H), 4.84 (d, J=9.5 Hz, 1H), 3.95 (t, J=10.0 Hz, 1H), 3.69 (s, 3H), 3.63 (d, J=10.0 Hz, 1H), 3.33-3.27 (m, 1H), 3.30 (s, 3H), 3.09 (s, 3H), 2.90 (d, J=11.5 Hz, 1H), 2.84 (d, J=11.5 Hz, 1H), 2.71 (d, J=12.5 Hz, 1H), 2.38-2.37 (m, 1H), 2.18 (brs, 1H), 2.05 (s, 3H), 1.78-1.71 (m, 1H), 1.16 (s, 3H), 0.97 (d, J=5.5 Hz, 3H), 0.68 (d, J=6.0 Hz, 3H); MS (ESI) Calcd. for ($C_{36}H_{46}FN_3O_9$): 683, found 706 (MNa$^+$), 682 (M-H)$^-$.

Example 9

This example demonstrates the preparation of 18-N-(3,4-Dichloro)benzamide-21-hydroxylgeldanamycin (9)

Compounds 9 (102.7 mg, 62.8% yield) as pale solid was prepared from 18-methoximino geldanamycin (0.222 mmol) and 3,4-dichlorobenzoyl chloride (37.3 mg, 0.178 mmol) in the same manner as described for 1.

$^1$H NMR (9, MeOD, 500 MHz) δ 8.07 (d, J=1.5, 1H), 7.88 (s, 1H), 7.85 (dd, J=1.5 and 8.5 Hz, 1H), 7.77 (d, J=8.0 Hz, 1H), 6.43 (t, J=11.5 Hz, 1H), 6.17 (d, J=11.5 Hz, 1H), 5.13-5.05 (m, 2H), 4.83 (d, J=9.5 Hz, 1H), 3.96 (t, J=9.5 Hz, 1H), 3.69 (s, 3H), 3.63 (d, J=9.5 Hz, 1H), 3.32-3.28 (m, 1H), 3.30 (s, 3H), 3.09 (s, 3H), 2.92-2.89 (m, 1H), 2.85-2.83 (m, 1H), 2.72 (d, J=12.5 Hz, 1H), 2.39-2.35 (m, 1H), 2.19-2.17 (m, 1H), 2.05 (s, 3H), 1.78-1.70 (m, 1H), 1.14 (s, 3H), 0.97 (d, J=6.0 Hz, 3H), 0.68 (d, J=5.5 Hz, 3H); MS (ESI) Calcd. for ($C_{36}H_{45}Cl_2N_3O_9$): 733, found 756 (MNa$^+$), 732 (M-H)$^-$.

Example 10

This example demonstrates the preparation of 18-N-(2-Furo)amide-21-hydroxylgeldanamycin (10)

Compounds 10 (69.5 mg, 49.0% yield) as pale solid was prepared from 18-methoximino geldanamycin (0.216 mmol) and 2-furoyl chloride (22.6 mg, 0.173 mmol) in the same manner as described for 1.

$^1$H NMR (10, CDCl$_3$, 500 MHz) δ 8.81 (s, 1H), 8.74 (brs, 1H), 8.64 (brs, 1H), 8.48 (s, 1H), 7.49 (s, 1H), 7.22 (d, J=3.0 Hz, 1H), 6.92 (d, J=10.5 Hz, 1H), 5.76 (d, J=8.5 Hz, 1H), 5.71 (t, J=10.0 Hz, 1H), 5.70 (d, J=8.0 Hz, 1H), 5.39-5.31 (m, 2H), 5.02 (s, 1H), 4.29 (d, J=9.0 Hz, 1H), 3.69 (s, 3H), 3.53 (d, J=8.5 Hz, 1H), 3.43-3.41 (m, 1H), 3.33 (s, 3H), 3.22 (s, 3H), 2.80-2.67 (m, 3H), 2.52 (d, J=12.0 Hz, 1H), 1.87 (s, 3H), 1.83-1.81 (m, 2H), 1.74 (s, 3H), 1.69-1.66 (m, 1H), 0.94 (d, J=4.0 Hz, 3H), 0.84 (d, J=6.0 Hz, 3H); MS (ESI) Calcd. for ($C_{34}H_{45}N_3O_{10}$): 655, found 678 (MNa$^+$), 654 (M-H)$^-$.

Example 11

This example demonstrates the preparation of 18-N-iso-Nicotinamide-21-hydroxylgeldanamycin (11)

A solution of 18-methoximino geldanamycin (108.0 mg, 0.183 mmol) in EtOAc was treated with Na$_2$S$_2$O$_4$ at RT. After 3 h, the aqueous layer was extracted twice with EtOAC and the combined organic layers were dried over Na$_2$S$_2$O$_4$, concentrated under reduced pressure to give 18-amino-21-hydroxylgeldanamycin as yellow solid. This latter was dissolved into anhydrous CH$_2$Cl$_2$ under argon atmosphere and to the resulting solution was added iso-nicotinoyl chloride hydrochloride (26.0 mg, 0.146 mmol) and triethylamine (18.5 mg, 0.183 mmol) at 0° C. After 12 h at RT, the reaction mixture was diluted with CH$_2$Cl$_2$, washed with sat. NaHCO$_3$, and dried over Na$_2$SO$_4$, after filtration and removed the solvent under reduced pressure, the crude product was purified by flash chromatography to give 11 as pale solid (85.0 mg, yield 69.7%). $^1$H NMR (11, MeOD, 500 MHz) δ 8.79 (d, J=5.0 Hz, 2H), 7.95 (s, 1H), 7.89 (d, J=5.0 Hz, 2H), 6.43 (t, J=11.5 Hz, 1H), 6.17 (d, J=11.5 Hz, 1H), 5.13-5.06 (m, 2H), 4.84 (d, J=9.0 Hz, 1H), 3.95 (t, J=10.0 Hz, 1H), 3.70 (s, 3H), 3.62 (d, J=10.0 Hz, 1H), 3.32-3.27 (m, 1H), 3.30 (s, 3H), 3.09 (s, 3H), 2.91 (d, J=10.5 Hz, 1H), 2.84 (d, J=11.0 Hz, 1H), 2.72 (d, J=12.0 Hz, 1H), 2.37-2.36 (m, 1H), 2.18 (brs, 1H), 2.05 (s, 3H), 1.75-1.71 (m, 1H), 1.15 (s, 3H), 0.96 (d, J=5.5 Hz, 3H), 0.68 (d, J=6.0 Hz, 3H); MS (ESI) Calcd. for ($C_{35}H_{46}N_4O_9$): 666, found 689 (MNa$^+$), 665 (M-H)$^-$.

Example 12

This example demonstrates the preparation of 18-N-Acrylamide-21-hydroxylgeldanamycin (12)

Compounds 12 (60.6 mg, 53.8% yield) as pale solid was prepared from 18-methoximino geldanamycin (0.183 mmol) and acryloyl chloride (9.94 mg, 0.110 mmol) in the same manner as described for 1.

$^1$H NMR (12, MeOD, 500 MHz) δ 7.90 (s, 1H), 6.71-6.65 (m, 1H), 6.40 (d, J=13.0 Hz, 2H), 6.12 (d, J=10.5 Hz, 1H), 5.83 (d, J=9.0 Hz, 1H), 5.13 (d, J=10.0 Hz, 1H), 5.09-5.02 (m, 1H), 4.83 (dd, J=4.0 and 9.25 Hz, 1H), 3.94-3.90 (m, 1H), 3.62 (s, 3H), 3.62-3.61 (m, 1H), 3.30 (s, 4H), 3.09 (s, 3H), 2.89-2.83 (m, 2H), 2.69 (d, J=13.0 Hz, 1H), 2.39-2.38 (m, 1H), 2.18 (d, J=4.0 Hz, 1H), 2.04 (s, 3H), 1.77-1.71 (m, 1H), 1.10 (s, 3H), 1.00 (brs, 3H), 0.67 (brs, 3H); MS (ESI) Calcd. for ($C_{32}H_{45}N_3O_9$): 615, found 638 (MNa$^+$), 614 (M-H)$^-$.

Example 13

This example demonstrates the preparation of 18-N-Benzylcarbamate-21-hydroxylgeldanamycin (16)

Compounds 16 (54.7 mg, 37.5% yield) as pale solid was prepared from 18-methoximino geldanamycin (0.214 mmol) and phenyl chloroformate (26.8 mg, 0.171 mmol) in the same manner as described for 1.

¹H NMR (16, MeOD, 500 MHz) δ 7.66 (s, 1H), 7.46 (t, J=8.0 Hz, 2H), 7.29 (t, J=7.5 Hz, 1H), 7.24 (d, J=8.0 Hz, 2H), 6.42 (t, J=11.5 Hz, 1H), 6.12 (d, J=11.5 Hz, 1H), 5.15 (d, J=10.5 Hz, 1H), 5.06 (t, J=10.5 Hz, 1H), 4.85 (d, J=9.5 Hz, 1H), 3.95 (t, J=10.5 Hz, 1H), 3.67 (s, 3H), 3.65 (d, J=11.0 Hz, 1H), 3.33-3.31 (m, 1H), 3.31 (s, 3H), 3.09 (s, 3H), 2.91-2.84 (m, 2H), 2.70 (d, J=11.0 Hz, 1H), 2.42-2.40 (m, 1H), 2.18 (brs, 1H), 2.03 (s, 3H), 1.78-1.74 (m, 1H), 1.21 (s, 3H), 1.02 (d, J=6.5 Hz, 3H), 0.67 (d, J=6.5 Hz, 3H); MS (ESI) Calcd. for ($C_{36}H_{47}N_3O_{10}$): 681, found 704 (MNa⁺), 680 (M-H)⁻.

Example 14

This example demonstrates the preparation of 18-N-(4-trifluoromethylbenzene)sulfamide-21-hydroxylgeldanamycin (29)

Compounds 29 (66.3 mg, 40.3% yield) as yellow solid was prepared from 18-methoximino geldanamycin (0.214 mmol) and 4-trifluoromethylbenzenesulfonyl chloride (41.8 mg, 0.171 mmol) in the same manner as described for 1.

¹H NMR (HH29, MeOD, 500 MHz) δ 8.02 (d, J=8.0 Hz, 2H), 7.86 (d, J=8.5 Hz, 2H), 7.44 (s, 1H), 6.40 (t, J=11.5 Hz, 1H), 6.16 (d, J=11.5 Hz, 1H), 5.14 (d, J=10.5 Hz, 1H), 5.07 (t, J=11.0 Hz, 1H), 4.85 (d, J=9.5 Hz, 1H), 3.98 (t, J=10.5 Hz, 1H), 3.61 (d, J=10.5 Hz, 1H), 3.38-3.32 (m, 1H), 3.27 (s, 3H), 3.11 (s, 3H), 2.86 (s, 3H), 2.81-2.75 (m, 2H), 2.47 (d, J=11.0 Hz, 1H), 2.34-2.29 (m, 1H), 2.08 (brs, 1H), 2.02 (s, 3H), 1.78 (brs, 1H), 1.19 (s, 3H), 0.99 (d, J=6.0 Hz, 3H), 0.61 (d, J=6.5 Hz, 3H); MS (ESI) Calcd. for ($C_{36}H_{46}F_3N_3O_{10}S$): 769, found 792 (MNa⁺), 768 (M-H)⁻.

Example 15

This example demonstrates the preparation of 18-N-Benzylurea-21-hydroxylgeldanamycin (49)

Compounds 49 (56.3 mg, 38.2% yield) as pale solid was prepared from 18-methoximino geldanamycin (0.216 mmol) and phenyl isocyanate (28.2 mg, 0.178 mmol) in the same manner as described for 1.

¹H NMR (HH44, MeOD, 500 MHz) δ 7.78 (s, 1H), 7.49 (d, J=8.0 Hz, 2H), 7.32 (t, J=7.5 Hz, 2H), 7.04 (t, J=7.5 Hz, 1H), 6.42 (t, J=11.5 Hz, 1H), 6.14 (d, J=11.5 Hz, 1H), 5.13 (d, J=10.5 Hz, 1H), 5.09-5.02 (m, 1H), 4.83 (d, J=9.5 Hz, 1H), 3.95 (t, J=10.0 Hz, 1H), 3.68 (s, 3H), 3.63 (d, J=10.0 Hz, 1H), 3.32 (s, 1H), 3.30 (s, 3H), 3.09 (s, 3H), 2.92-2.89 (m, 2H), 2.68 (d, J=11.5 Hz, 1H), 2.40-2.35 (m, 1H), 2.18 (brs, 1H), 2.04 (s, 3H), 1.78-1.73 (m, 1H), 1.19 (s, 3H), 1.00 (d, J=6.5 Hz, 3H), 0.68 (d, J=6.5 Hz, 3H); MS (ESI) Calcd. for ($C_{36}H_{48}N_4O_9$): 680, found 703 (MNa⁺), 679 (M-H)⁻.

Example 16

This example demonstrates the preparation of 18-N-(3,4-Dichloro)benzamide-21-methoxylgeldanamycin (70)

To a solution of HH129 (50.0 mg, 0.068 mmol) in 1 mL DMF was added NaH (2.7 mg, 0.068 mmol). The mixture was stirred at room temperature for 90 min. To the resulting solution was added MeI (15.4 mg, 0.109 mmol) at 0° C. After 12 h at RT, the reaction mixture was diluted with EtOAc, washed with water, combined the organic layer and dried over $Na_2SO_4$, after filtration and removed the solvent under reduced pressure, the crude product was purified by flash chromatography to give 70 as pale solid (40.0 mg, yield 78.5%). ¹H NMR (70, $CD_2Cl_2$, 500 MHz) δ 8.38 (s, 1H), 8.23 (s, 1H), 7.99 (s, 1H), 7.93 (s, 1H), 7.67 (dd, J=2.0 and 8.25 Hz, 1H), 7.63 (s, 1H), 6.33 (t, J=11.5 Hz, 1H), 6.08 (d, J=11.5 Hz, 1H), 5.07 (d, J=10.5 Hz, 1H), 5.00 (t, J=11.0 Hz, 1H), 4.81 (d, J=10.0 Hz, 1H), 4.75-4.68 (m, 2H), 3.80-3.73 (m, 1H), 3.76 (s, 3H), 3.57 (d, J=10.0 Hz, 1H), 3.51 (s, 3H), 3.31 (s, 1H), 3.26 (s, 3H), 3.09 (s, 3H), 2.76-2.72 (m, 2H), 2.67-2.64 (m, 1H), 2.19-2.12 (m, 1H), 1.97 (s, 3H), 1.61-1.55 (m, 2H), 0.96 (s, 3H), 0.93 (d, J=6.0 Hz, 3H), 0.59 (d, J=6.5 Hz, 3H); MS (ESI) Calcd. for ($C_{37}H_{47}Cl_2N_3O_9$): 747, found 770 (MNa⁺), 746 M-H)⁻.

Example 17

This example demonstrates the in vitro growth inhibition for certain compounds of the invention on MX-1 (human breast carcinoma) cells.

A cytotoxicity assay was quantitated using the Promega CellTiter Blue Cell Viability Assay. Briefly, cells (5000 cells/well) were plated onto 96-well microtiter plates in RPMI 1640 medium supplemented with 10% FBS and incubated at 37° C. in a humidified 5% $CO_2$ atmosphere. After 24 hrs., cells were exposed to various concentrations of compound in DMSO and cultured for another 72 hrs. 100 ul of media were removed and 20 ul of Promega CellTiter Blue reagent were added to each well and shaken to mix. After 4 hours of incubation at 37° C. in a humidified 5% $CO_2$ atmosphere, the plates were read at 544ex/620em. The fluorescence produced is proportional to the number of viable cells. After plotting fluorescence produced against drug concentration, the $IC_{50}$ was calculated as the half-life of the resulting non-linear regression. The data is presented in Table 2.

TABLE 2

Cytotoxicity of geldanamycin analogs

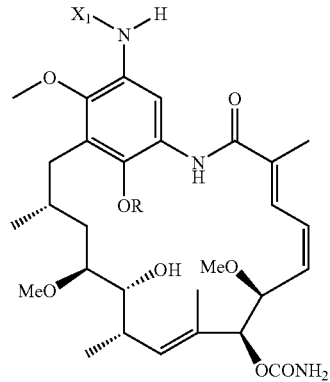

| ID | $X_1$ | R | IC50, μM MX-1 |
|---|---|---|---|
| GA | $OCH_3$ | H | 0.5 |
| 17-AAG | $NHCH_2CH=CH_2$ | H | 1.7 |
| 1 | 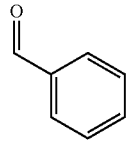 | H | 1.9 |

TABLE 2-continued
Cytotoxicity of geldanamycin analogs
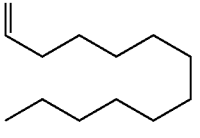
| ID | X₁ | R | IC50, μM MX-1 |
|---|---|---|---|
| 2 | 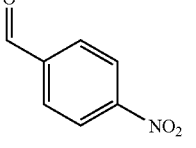 | H | 1.3 |
| 3 | 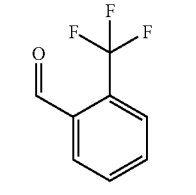 | H | 0.42 |
| 4 | 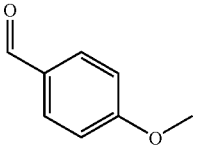 | H | 0.68 |
| 5 | 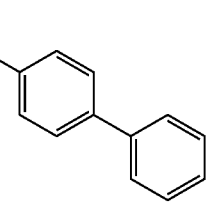 | H | 0.29 |
| 6 | 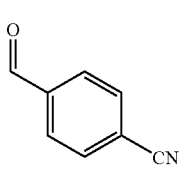 | H | 0.081 |
| 7 | 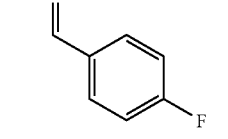 | H | 0.13 |
TABLE 2-continued
Cytotoxicity of geldanamycin analogs
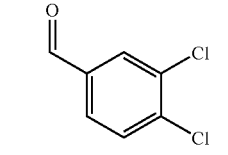
| ID | X₁ | R | IC50, μM MX-1 |
|---|---|---|---|
| 8 | 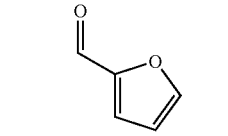 | H | 2.0 |
| 9 | 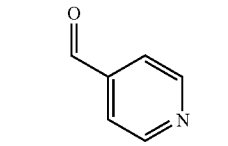 | H | 0.80 |
| 10 | 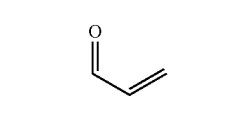 | H | 7.2 |
| 11 | 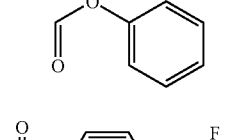 | H | 0.10 |
| 12 | 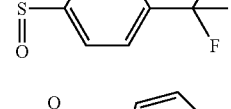 | H | 15.3 |
| 16 | 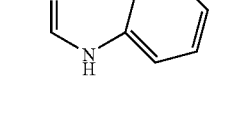 | H | 0.088 |
| 29 |  | H | 0.078 |
| 49 |  | H | 2.4 |

TABLE 2-continued

Cytotoxicity of geldanamycin analogs

| | Substituents | | IC50, µM |
|---|---|---|---|
| ID | X₁ | R | MX-1 |
| 70 | (3,4-dichlorobenzaldehyde) | CH3 | 12.4 |

Obviously, numerous modifications and variations of the present invention are possible in light of the above teachings. It is therefore to be understood that within the scope of the appended claims, the invention may be practiced otherwise than as specifically described herein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A compound or pharmaceutically acceptable salt thereof having the formula (I)

(I)

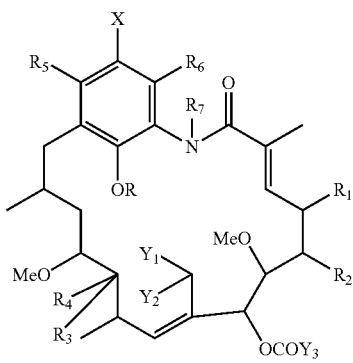

wherein

X is selected from the group consisting of —N($R_8$)($R_9$), —N($R_8$)—C(O)$R_{10}$, —N($R_8$)—C(O)—O$R_{10}$, —N($R_8$)—SO$_2$$R_{10}$, —N($R_8$)—C(O)—N$R_8$$R_{10}$, —N($R_8$)—C(S)O$R_{10}$, —N($R_8$)—C(S)—O$R_{10}$, and —N($R_8$)—C(S)—N$R_8$$R_{10}$;

wherein $R_8$ and $R_9$ are independently selected from the group consisting of H, ($C_1$-$C_{20}$) alkyl, ($C_2$-$C_{20}$) alkenyl, ($C_2$-$C_{20}$) alkynyl, optionally substituted aryl, optionally substituted heteroaryl, optionally substituted arylalkyl, optionally substituted heteroarylalkyl, cycloalkyl, and heterocyclic alkyl;

$R_8$ is selected from the group consisting of H, ($C_1$-$C_6$) alkyl, optionally substituted ($C_5$-$C_8$) aryl, and an optionally substituted ($C_5$-$C_8$) heteroaryl, or together with $R_9$ forms a 4-7 membered heterocyclic ring;

$R_{10}$ is selected from the group consisting of hydrogen, ($C_1$-$C_{20}$) alkyl, ($C_2$-$C_{20}$) alkenyl, ($C_2$-$C_{20}$) alkynyl, optionally substituted ($C_6$-$C_{20}$) aryl, optionally substituted ($C_3$-$C_{20}$) heteroaryl, optionally substituted ($C_7$-$C_{20}$) arylalkyl, optionally substituted ($C_4$-$C_{20}$) heteroarylalkyl, ($C_3$-$C_{20}$) cycloalkyl, and a ($C_2$-$C_{20}$) alicyclic heterocyclyl;

R represents, hydrogen, ($C_1$-$C_6$) alkyl or ($C_1$-$C_6$) alkenyl or ($C_6$-$C_{10}$) aryl or OCOR$_{10}$;

$R_1$ and $R_2$ are each a hydrogen or $R_1$ and $R_2$ together form a single bond;

$R_3$, $R_4$, $Y_1$, $Y_2$, $Y_3$ are independently selected from the group consisting H, halo, —OH, O-alkyl, O-acetyl, —O-aryl, OC(O)$R_{10}$, —SO$_2$—$R_{10}$, and —NHR$_{10}$, or together form oxo (=O), or hydroxylamino alkoxyimine or aryloxyimine, thioketo; or $R_3$ and $R_4$ or $Y_1$ and $Y_2$ form a heterocyclic group selected from the group consisting of aziridinyl, azetidinyl, pyrrolidinyl, piperidinyl, thiazolidinyl, oxazolidinyl, morpholino, piperazinyl, 4-($C_1$-$C_4$) alkylpiperidinyl and N—($C_1$-$C_4$) piperazinyl; and said groups may be substituted with one or more groups selected from the group consisting of ($C_1$-$C_8$) alkyl, halo, nitro, amino, azido and ($C_1$-$C_8$) alkoxyl;

$R_5$ is selected from the group consisting of a ($C_1$-$C_{20}$) alkyl, ($C_2$-$C_{20}$) alkenyl, ($C_2$-$C_{20}$) alkynyl, optionally substituted ($C_6$-$C_{20}$) aryl, optionally substituted ($C_3$-$C_{20}$) heteroaryl, optionally substituted ($C_7$-$C_{20}$) arylalkyl, optionally substituted ($C_4$-$C_{20}$) heteroarylalkyl, ($C_3$-$C_{20}$) cycloalkyl, ($C_2$-$C_{20}$) alicyclic heterocyclyl, $N(R_8)(R_9)$; —$OR_{10}$, —$SR_{10}$, —$N(R_8)$—$C(O)R_{10}$, —$N(R_8)$—$C(O)$—$OR_{10}$, —$N(R_8)$—$C(O)$—$NR_8R_{10}$, —$N(R_8)$—$C(S)OR_{10}$, —$N(R_8)$—$C(S)$—$OR_{10}$, and —$N(R_8)$—$C(S)$—$NR_8R_{10}$, $R_6$ is selected from the group consisting of, hydrogen, hallo, a ($C_1$-$C_{10}$) alkyl, ($C_1$-$C_{10}$) alkenyl, or an optionally substituted or unsubstituted ($C_6$-$C_{10}$) aryl; and $R_7$ is selected from the group consisted of hydrogen, a ($C_1$-$C_{10}$) alkyl, optionally substituted ($C_5$-$C_{10}$) aryl and ($C_1$-$C_{10}$) acyl.

2. The compound of claim 1 wherein, X is selected from $N(R_8)(R_9)$, —$N(R_8)$—$C(O)R_{10}$, —$N(R_8)$—$C(O)$—$OR_{10}$, —$N(R_8)$—$C(O)$—$NR_8R_{10}$, —$N(R_8)$—$SO_2R_{10}$, —$N(R_8)$—$C(S)$—$OR_{10}$, and —$N(R_8)$—$C(S)$—$NR_8R_{10}$.

3. The compound of claim 1 wherein the compound is:

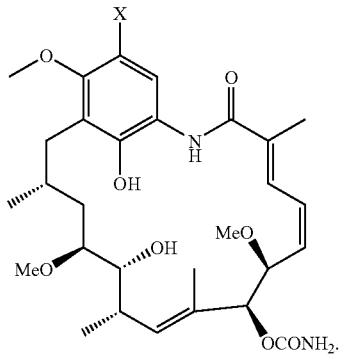

4. The compound of claim 3, wherein X is selected from the group consisting of —$N(R_8)$—$C(O)R_{10}$, $N(R_8)$—$C(O)$—$OR_{10}$, —$N(R_8)$—$SO_2R_{10}$, —$N(R_8)$—$C(O)$—$NR_8R_{10}$, —$N(R_8)$—$C(S)OR_{10}$, —$N(R_8)$—$C(S)OR_{10}$, —$N(R_8)$—$C(S)$—$NR_8R_{10}$, and —$N(R_8)(R_9)$.

5. The compound of claim 4, wherein $R_8$ is hydrogen.

6. The compound of claim 4, wherein $R_8$ is methyl.

7. The compound of claim 4, wherein $R_{10}$ is ($C_6$-$C_{10}$) aryl.

8. The compound of claim 5, wherein $R_{10}$ is ($C_6$-$C_{10}$) aryl.

9. The compound of claim 6, wherein $R_{10}$ is ($C_6$-$C_{10}$) aryl.

10. A pharmaceutical composition comprising the compound of claim 1 and a pharmaceutically acceptable carrier.

11. The pharmaceutical composition of claim 1, wherein the composition is suitable for delivery via routes of administration selected from the group consisting of oral, parenteral, intravenous, and combinations thereof.

12. The pharmaceutical composition of claim 11, wherein said composition is suitable for oral delivery and further comprises one or more ingredients selected from the group consisting of a diluent, an edible carrier, a binder, an excipient, a disintegrating agent, a lubricant, a glidant, and a sweetening agent.

13. The pharmaceutical composition of claim 11 wherein said composition is suitable for parenteral delivery and comprises one or more ingredients selected from the group consisting of a sterile diluent, antimicrobial agents, antioxidants, buffers, tonicity adjusting agents.

* * * * *